(12) United States Patent
Ramirez et al.

(10) Patent No.: US 11,852,640 B2
(45) Date of Patent: Dec. 26, 2023

(54) HEMATOLOGY ANALYZERS AND METHODS OF OPERATION

(71) Applicant: Beckman Coulter, Inc., Brea, CA (US)

(72) Inventors: Carlos Ramirez, Miami, FL (US); Nery Ortiz, Miami, FL (US); Milton Swaby, Pembroke Pines, FL (US)

(73) Assignee: Beckman Coulter, Inc., Brea, CA (US)

( * ) Notice: Subject to any disclaimer, the term of this patent is extended or adjusted under 35 U.S.C. 154(b) by 1245 days.

(21) Appl. No.: 16/170,389

(22) Filed: Oct. 25, 2018

(65) Prior Publication Data

US 2019/0128906 A1 May 2, 2019

Related U.S. Application Data

(60) Provisional application No. 62/578,239, filed on Oct. 27, 2017.

(51) Int. Cl.
*G01N 35/00* (2006.01)
*G01N 15/10* (2006.01)
(Continued)

(52) U.S. Cl.
CPC ... *G01N 35/00623* (2013.01); *G01N 15/0205* (2013.01); *G01N 15/1012* (2013.01);
(Continued)

(58) Field of Classification Search
CPC ......... G01N 35/00623; G01N 15/0205; G01N 15/1012; G01N 15/1031; G01N 15/1459;
(Continued)

(56) References Cited

U.S. PATENT DOCUMENTS 5,125,737 A   6/1992   Rodriguez et al.
5,341,291 A   8/1994   Roizen, III et al.
(Continued)

FOREIGN PATENT DOCUMENTS

CN   102033035 B   11/2013
EP   1021701       7/2000
(Continued)

OTHER PUBLICATIONS

Cembrowski et al., "Rationale for using insensitive quality control rules for today's hematology analyzers", 2010, Int. Jnl. Lab. Hem., 32, 606-615. (Year: 2010).*

(Continued)

*Primary Examiner* — Samuel P Siefke
*Assistant Examiner* — Henry H Nguyen
(74) *Attorney, Agent, or Firm* — Frost Brown Todd LLP

(57) ABSTRACT

Instances of the present technology may include a method for operating a hematology analyzer. The method may include passing a control material through a hematology analyzer. The control material may include a first cell population and a second cell population. The method may also include determining a first cell population volume measurement and a second cell population volume measurement. A first value of a first cell population distribution width and a second value of a second cell population distribution width may be calculated. The method may include comparing the first value to a first reference range. The method may also include comparing the second value to a second reference range. Furthermore, the method may include classifying an operational status of the hematology analyzer based on the comparison of the first value to the first reference range and based on the comparison of the second value to the second reference range.

23 Claims, 8 Drawing Sheets

(51) Int. Cl.

| | |
|---|---|
| *G01N 15/14* | (2006.01) |
| *G01N 15/02* | (2006.01) |
| *G01N 33/49* | (2006.01) |
| *G01N 15/00* | (2006.01) |
| *G16H 40/40* | (2018.01) |
| *G16H 10/40* | (2018.01) |
| *G16H 40/60* | (2018.01) |
| *G16H 50/20* | (2018.01) |

(52) U.S. Cl.
CPC ..... *G01N 15/1031* (2013.01); *G01N 15/1459* (2013.01); *G01N 33/4915* (2013.01); *G01N 35/00693* (2013.01); *G16H 10/40* (2018.01); *G16H 40/40* (2018.01); *G16H 40/60* (2018.01); *G16H 50/20* (2018.01); *G01N 2015/008* (2013.01); *G01N 2015/0069* (2013.01); *G01N 2015/0073* (2013.01); *G01N 2015/0084* (2013.01); *G01N 2015/1006* (2013.01); *G01N 2015/1087* (2013.01); *G01N 2015/1402* (2013.01); *G01N 2015/1493* (2013.01)

(58) Field of Classification Search
CPC ......... G01N 33/4915; G01N 35/00693; G01N 2015/0069; G01N 2015/0073; G01N 2015/008; G01N 2015/0084; G01N 2015/1006; G01N 2015/1087; G01N 2015/1402; G01N 2015/1493; G16H 10/40; G16H 40/40; G16H 40/60; G16H 50/20
See application file for complete search history.

(56) References Cited

U.S. PATENT DOCUMENTS

| | | | |
|---|---|---|---|
| 5,529,933 A | 6/1996 | Young et al. | |
| 6,228,652 B1 | 5/2001 | Rodriguez et al. | |
| 6,509,192 B1* | 1/2003 | Young | G01N 33/96 |
| | | | 436/15 |
| 7,109,036 B2 | 9/2006 | Ortiz et al. | |
| 7,135,341 B2 | 11/2006 | Ortiz et al. | |
| 7,176,031 B2 | 2/2007 | Li et al. | |
| 7,195,919 B2 | 3/2007 | Jacobs et al. | |
| 7,285,417 B2 | 10/2007 | Ortiz et al. | |
| 7,390,662 B2 | 6/2008 | Riley et al. | |
| 7,393,688 B2 | 7/2008 | Ortiz et al. | |
| 8,094,299 B2 | 1/2012 | Wells et al. | |
| 8,189,187 B2 | 5/2012 | Graham et al. | |
| 8,221,995 B2 | 7/2012 | Lee et al. | |
| 8,719,053 B2 | 5/2014 | Showalter et al. | |
| 9,939,453 B2 | 4/2018 | Lu et al. | |
| 10,221,453 B2 | 3/2019 | Shi et al. | |
| 2001/0051879 A1 | 12/2001 | Johnson et al. | |
| 2001/0051880 A1 | 12/2001 | Schurenberg et al. | |
| 2003/0105648 A1 | 6/2003 | Schurenberg et al. | |
| 2004/0042471 A1 | 3/2004 | Yung et al. | |
| 2004/0220761 A1 | 11/2004 | Yundt-Pacheco | |
| 2004/0267562 A1 | 12/2004 | Fuhrer et al. | |
| 2005/0022103 A1 | 1/2005 | Yundt-Pacheco | |
| 2005/0159982 A1 | 7/2005 | Showalter et al. | |
| 2008/0186134 A1 | 8/2008 | Parkhurst et al. | |
| 2009/0149724 A1 | 6/2009 | Mark et al. | |
| 2011/0046910 A1 | 2/2011 | Haas et al. | |
| 2011/0076685 A1 | 3/2011 | Moeller et al. | |
| 2011/0166794 A1 | 7/2011 | Linssen et al. | |
| 2012/0109531 A1 | 5/2012 | Knafel et al. | |
| 2012/0109682 A1 | 5/2012 | Seltzer et al. | |
| 2013/0123131 A1* | 5/2013 | Purvis | C12Q 1/025 |
| | | | 506/10 |
| 2013/0197943 A1 | 8/2013 | Conlin et al. | |
| 2013/0246079 A1 | 9/2013 | Hoffman et al. | |
| 2014/0084930 A1 | 6/2014 | Han | |
| 2014/0160464 A1* | 6/2014 | Han | G01N 33/4915 |
| | | | 356/39 |
| 2014/0172321 A1 | 6/2014 | Han | |
| 2015/0338427 A1 | 11/2015 | Pollack et al. | |
| 2016/0168638 A1 | 6/2016 | Garrett et al. | |
| 2016/0356801 A1 | 12/2016 | Glavina et al. | |
| 2017/0285624 A1* | 10/2017 | Lesher | G05B 19/41875 |
| 2019/0324035 A1 | 10/2019 | Magari et al. | |
| 2019/0324036 A1 | 10/2019 | Xin et al. | |
| 2019/0348182 A1 | 11/2019 | Magari et al. | |
| 2019/0362824 A1 | 11/2019 | Xin et al. | |
| 2019/0383800 A1 | 12/2019 | Careaga et al. | |
| 2021/0007675 A1 | 1/2021 | Tejidor et al. | |
| 2021/0010924 A1 | 1/2021 | Tejidor et al. | |
| 2021/0011005 A1 | 1/2021 | Tejidor et al. | |

FOREIGN PATENT DOCUMENTS

| | | |
|---|---|---|
| EP | 1718966 | 11/2006 |
| JP | 2012-529033 A | 11/2012 |
| KR | 20150036329 A | 4/2015 |
| KR | 20150091049 A | 8/2015 |
| WO | WO 88/07198 A1 | 9/1988 |
| WO | WO 2004/044556 A2 | 5/2004 |
| WO | WO 2012/139047 A2 | 10/2012 |
| WO | WO 2014/028534 A2 | 2/2014 |
| WO | WO 2014/084930 | 6/2014 |
| WO | WO 2014/154810 A1 | 10/2014 |
| WO | 2017/132132 A1 | 8/2017 |
| WO | WO 2019/028448 A1 | 2/2019 |

OTHER PUBLICATIONS

Goyette, et al., "Hematologic changes in sepsis and their therapeutic implications," Seminars in Respiratory and Critical Care Medicine, vol. 25, No. 6, pp. 645-659 (2004).

Kaukonen, et al., "Systemic Inflammatory Response Syndrome Criteria in Defining Severe Sepsis," New England Journal of Medicine, 372: 1629-38, Apr. 23, 2015, (doi:610.1056/NEJMoal415236).

Singer, et al., "The Third International Consensus Definitions for Sepsis and Septic Shock (Sepsis-3)," JAMA, 10 315(8): 801-810, Feb. 23, 2016.

Warner, "Tips for evaluating a peripheral blood smear for possible sepsis," Jan. 15, 2013, 3 pages, available at laboratorian.advanceweb.com/signs-of-sepsis/.

International Search Report and Written Opinion dated May 4, 2018 for International Application No. PCT/US2018/020087, 13 pages.

International Search Report and Written Opinion dated Mar. 26, 2019 for International Application No. PCT/US2018/057645, 16 pages.

International Search Report and Written Opinion dated Aug. 2, 2019 for International Application No. PCT/US2019/028487, 7 pages.

International Search Report and Written Opinion dated Aug. 20, 2019 for International Application No. PCT/US2019/031151, 9 pages.

International Search Report and Written Opinion dated Sep. 4, 2019 for International Application No. PCT/US2019/028486, 11 pages.

U.S. Appl. No. 16/488,503, entitled "Cross Discipline Disease Management System," filed Aug. 23, 2019.

Aird; William C., "The Hematologic System as a Marker of Organ Dysfunction in Sepsis", Mayo Clin Proc., Jul. 2003;78:869-881, *2003 Mayo Foundation for Medical Education and Research*.

"Early Sepsis Indicator Application Addendum UniCel DxH 900 Coulter Cellular Analysis System", Beckman Coulter, published Version: v1, Available online at: https://www.analis.be/site/objects/media/0/0/8/1/9/0081990_media/media1.pdf, Apr. 26, 2018, 38 pages.

"UniCel DxH 800—Coulter Cellular Analysis System", Available online at: https://www.udh.med.sa/advices/DxH_operator_Manual.pdf, Aug. 5, 2017, 54 pages.

Vis, et al., "Verification and Quality Control of Routine Hematology Analyzers", International Journal of Laboratory Hematology, vol. 38, No. 1, May 9, 2016, pp. 100-109.

(56) References Cited

OTHER PUBLICATIONS

"Biomarker," The Pharmaceutical Society of Japan, a pharmaceutical science glossary, 2008, 2 pgs.
"Red Blood Cell Distribution With (RDW): Definition and Calculation—LabCE.com, Laboratory Continuing Education," Nov. 2012, downloaded Aug. 22, 2019 from: https://labce.com/spg579122_red_blood_cell_distribution_width_rdw_definition_a.aspx, 1 pg.
Sukhacheva, et al., "The Role of Monocytes in the Progression of Sepsis," Beckman Coulter, 2018, downloaded Aug. 22, 2019 from: media.beckmancoulter.com/-/media/diagnostics/products/hematology/early-sepsis-indicator/docs/role-of-monocytes-for-progression-of-sepsis-en.pdf, 12 pgs.
Zhou, et al., "VCS parameters of neutrophils, monocytes and lymphocytes may indicate local bacterial infection in cancer patients who accepted cytotoxic chemotherapeutics," Eur J Clin Microbiol Infect Dis, 2016, 35:41-48, 8 pgs.
Zonneveld, R., et al., "Analyzing Neutrophil Morphology, Mechanics, and Motility in Sepsis: Options and Challenges for Novel Bedside Technologies," Crit Care Med, 2016, 44(1):218-228, 11 pgs.
European Examination Report dated Oct. 15, 2020 for Application No. EP 17704357.7, 10 pgs.
International Search Report and Written Opinion dated Aug. 23, 2019 for International Application No. PCT/US2019/028488, 10 pgs.
International Search Report and Written Opinion dated Oct. 20, 2020 for International Application No. PCT/US2020/041535, 12 pgs.
International Search Report and Written Opinion dated Oct. 8, 2020 for International Application No. PCT/US2020/041548, 10 pgs.
International Search Report and Written Opinion dated Oct. 5, 2020 for International Application No. PCT/US2020/041541, 10 pgs.
Japanese Office Action, Notice of Reasons for Refusal, dated Oct. 29, 2020 JP 2018-538892, 27 pgs.
U.S. Office Action, Restriction Requirement, dated Apr. 7, 2021 for U.S. Appl. No. 15/987,541, 5 pgs.
U.S. Office Action, Non-Final Rejection, dated Jul. 31, 2020 for U.S. Appl. No. 16/073,757, 23 pgs.
U.S. Office Action, Notice of Allowance, dated Feb. 8, 2021 for U.S. Appl. No. 16/073,757, 20 pgs.
Park, D.H., "Screening of sepsis using 4 leukocyte cell population data from the Coulter automatic blood cell analyzer DxH800," Int. Jnl. Lab. Hem., 2011, 33, 391-399.
Anonymous, "Multiple Logistic Regression Analysis", Jan. 17, 2013, retrieved from http://sphweb.bumc.cu.edu/otlt/MPH-Modules/8S/8S704_Multivarialbe/8S704_Multivariables8.html.
Bhargava, et al. "Elevated mean neutrophil volume+ CRP is a highly sensitive and specific predictor of neonatal sepsis", Letter to the Editor, International Journal of Laboratory Hematology, DOI: 10.1111/iijh.12120, 2013, 4 pages.
Celik, et al., "Automated determination of neutrophil VCS parameters in diagnosis and treatment efficacy of neonatal sepsis", Pediatric Research, vol. 71, No. 1, Jan. 2012, pp. 121-125.
Chaves, et al. "Neutrophil Volume Distribution Width: A New Automated Hematologic Parameter for Acute Infection", Arch Pathoi Lab Med, vol. 130. Mar. 2006, pp. 378-380.
Chaves, et al. Quantitative Determination of Neutrophil VCS Parameters by the Coulter Automated Hematology Analyzer: New and Reliable Indicators for Acute Bacterial Infection. American Journal Clinical Pathology, 2005, 124:440-444, DOI, 10.1309/LLF75WOFWQQ8TCC5.
Cho, et al., "Biomarkers of Sepsis", Infection & Chemotherapy, Feb. 2014; 46:1-12.
Crouser, et al, "Imporved Early Detection of Sepsis in the ED with a Novel Monocyte Distribution Width Biomarker", 152#3 Chest, Sep. 2017, pp. 518-526.
Dellinger, et. al. "Surviving Sepsis Campaign: International Guidelines for Management of Severe Sepsis and Septic Shock, 2012", Intensive Care Medicine, 2013, 39:164-228, DOI 10.1007/s00134-012-2769-8.
Dilmoula, et al., "Volume Conductivity and Scatter Properties of Leukocytes (VCS Technology) in Detecting Sepsis in Critically Ill Adult Patients", Blood (ASH annual Meeting Abstracts) 2011; 118: Abstract 4729, 3 pages.
Ferrer, et al., "Emperic Antibiotic Treatment Reduces Mortality in Severe Sepsis and Septic Shock From the First Hour: Results From a Guideline-Based Performance Improvement Program", Critical Care Medicine, Aug. 2014, vol. 42, No. 8, pp. 1749-1755.
Gaieski, et al., "Impact of time to antibiotics on survival in patients with severe sepsis or septic shock in whom early goal-directed therapy was initiated in the emergency department", Critical Care Medicine, 2010, vol. 38, No. 4, pp. 1045-1053.
Garnacho-Montero, et al., "Impact of adequate empirical antibiotic therapy on the outcome of patients admitted to the intensive care unit with sepsis", Critical Care Medicine, 2003;31 :2742-51.
Gea-Banecloche, et al. "Sepsis associated with immunosuppressive medications: An evidence-based review" Critical Care Medicine 2004;32:S578-S590.
Glickman, et al., Disease Progression in Hemodynamically Stable Patients Presenting to the Emergency Department With Sepsis. Academic Emergency Medicine, vol. 17, Issue 4, Apr. 2, 2010, pp. 383-390.
Hou, et al., Viral infection triggers rapid differentiation of human blood monocytes into dendritic cells, *Blood* Mar. 29, 2012, vol. 119, No. 12, pp. 3128-3132.
Lee, et al., "Mean cell Volumes of neutrophils and monocytes are promising markers of sepsis in elderly patients", Blood Research, vol. 48, No. 3, Sep. 2013, 5 pages.
Levy, et al., "2001 SCCM/ESICM/ACCP/ATS/SIS Sepsis Definitions Conference", Critical Care Medicine, Mar. 28, 2003, 29: 530-538.
Liu, et al., "Hospital Deaths in Patients with Sepsis from 2 Independent Cohorts", *JAMA* Jul. 2, 2014; 312: 90-92.
Mardi, et al., Mean cell volume of neutrophils and monocytes compared with C-reactive protein, interleukin-6 and white blood cell count for prediction of sepsis and nonsystemic bacterial infections, accepted for publication, Sep. 23, 2009, International Journal of Laboratory Hematology 2010;32:410-418.
Park, et al, "Screening of sepsis using leukocyte cell population data from the Coulter automatic blood cell analyzer DxH800", Internatinal Journal of Laboratory Hematology, Dec. 6, 2010, 9 pages.
Raimondi, et al., "Automated Determination of Neutrophil Volume as Screening Test for Late-Onset Sepsis in Very Low Birth Infants", Pediatric Infectious Disease Journal, Feb. 2010;29:288-89.
Seymour, et al. "Severe Sepsis in Pre-Hospital Emergency Care: Analysis of Incidence, Care, and Outcome", American Journal of Respiritory Critical Care Medicine, Dec. 15, 2012; 186:1264-71.
Shalova, et al., "Human Monocytes Undergo Functional Reprogramming during Sepsis Mediated by Hypozia-Inducible Factor-1a", Immunity, Mar. 17, 2015; 42:484-98.
Skibsted, et al., "Bench-to-bedside review: Future novel diagnostics for sepsis—a systems biology approach", Critical Care Oct. 4, 2013;17:231, 15 pages.
Torio, et al "National Inpatient Hospital Costs: The Most Expensive Conditions by Payer, 2011", H-CUP US, Aug. 2013, 8 pages, retrieved from: https://www.hcup-us.ahrq.gov/reports/statbriefs/sb160.jsp.
PCT/US2017/014708 received an International Search Report and Written Opinion dated Apr. 20, 2017, 18 pages.
Beckman Coulter, "Coulter® 3-D VCS Technology," from <http://www.cyto.purdue.edu/cdroms/cyto2/6/coulter/ ss000125.htnn> (Year: 1996).
Beckman Coulter, Early Sepsis Indicator (ESId) Application for UniCel DxH 900 Series with System Manager Software, PN C26693AC (Jun. 2019), <https://www.beckmancoulter.corn/download/file/wsr-308328/C26693AC?type=pdf> (Year: 2019).
Beckman Coulter, Early Sepsis Indicator (ESId) Application Addendum, UniCel DxH 900 Series with System Manager Software Coulter Cellular Analysis System, PN C42014AC (Apr. 2020), <https://www.beckmancoulter.com/download/file/wsr-292218/C42014AC?type=pdf> (Year: 2020).

(56) References Cited

OTHER PUBLICATIONS

Beckman Coulter, UniCel DxH 900 Series with System Manager Software, PN B26647AG, <https://www.beckmancoulter.com/download/file/wsr-156667/B26647AG?type=pdf> (Year: 2020).

FDA 510(k) Substantial Equivalence Determination Decision Summary, <https://www.accessdata.fda.gov/cdrh_docs/reviews/K181599.pdf> (Year: 2018).

Nachimuthu, Senthil K., and Peter J. Haug. "Early detection of sepsis in the emergency department using Dynamic Bayesian Networks." *AMIA Annual Symposium Proceedings.* vol. 2012. American Medical Informatics Association, 2012.

Petrak, Russel M., et al. "The value of an infectious diseases specialist." *Clinical infectious diseases* 36.8 (2003): 1013-1017.

Chinese Office Action dated May 31, 2021, for Application No. 201780006733.8, 14 pages.

Chinese Office Action dated Mar. 9, 2022, for Application No. 201780006733.8, 4 pages.

European Examination Report dated Nov. 27, 2020, for Application No. 18712041.5, 11 pages.

European Examination Report dated Jul. 12, 2022, for Application No. 18845383.1. 13 pages.

Indian Office Action dated Jun. 25, 2021, for Application No. 201817031635, 7 pages.

Japanese Notification of Reasons for Refusal dated Feb. 4, 2022, for Application No. 2021-012832, 4 pages.

Japanese Notification of Reasons for Refusal dated Jun. 17, 2022, for Application No. 2021-012832, 2 pages.

Korean Office Action dated Aug. 27, 2021, for Application No. 10-2018-7024386, 27 pages.

U.S. Non-Final Rejection dated Jul. 9, 2021, for U.S. Appl. No. 15/987,541, 15 pages.

U.S. Final Rejection dated Feb. 17, 2022, for U.S. Appl. No. 15/987,541, 14 pages.

U.S. Notice of Allowance dated Sep. 1, 2022, for U.S. Appl. No. 15/987,541, 8 pages.

U.S. Restriction Requirement dated Mar. 14, 2022, for U.S. Appl. No. 16/390,597, 6 pages.

U.S. Non-Final Rejection dated Jun. 13, 2022, for U.S. Appl. No. 16/390,597, 8 pages.

U.S. Non-Final Rejection dated Jul. 2, 2021, for U.S. Appl. No. 16/390,633, 9 pages.

U.S. Non-Final Rejection dated Feb. 25, 2022, for U.S. Appl. No. 16/390,633, 13 pages.

U.S. Final Rejection dated Aug. 9, 2022, for U.S. Appl. No. 16/390,633, 11 pages.

U.S. Non-Final Rejection dated Jul. 9, 2021, for U.S. Appl. No. 16/390,648, 15 pages.

U.S. Final Rejection dated Feb. 17, 2022, for U.S. Appl. No. 16/390,648, 14 pages.

U.S. Notice of Allowance dated Jun. 15, 2022, for U.S. Appl. No. 16/390,648, 7 pages.

U.S. Restriction Requirement dated Jun. 16, 2021, for U.S. Appl. No. 16/488,503, 8 pages.

U.S. Non-Final Rejection dated Nov. 24, 2021, for U.S. Appl. No. 16/488,503, 21 pages.

U.S. Final Rejection dated Aug. 11, 2022, for U.S. Appl. No. 16/488,503, 21 pages.

U.S. Non-Final Rejection dated Jun. 23, 2022, for U.S. Appl. No. 16/925,933, 9 pages.

U.S. Restriction Requirement dated Aug. 8, 2022, for U.S. Appl. No. 16/925,937, 13 pages.

U.S. Restriction Requirement dated Oct. 5, 2022, for U.S. Appl. No. 16/925,943, 8 pages.

\* cited by examiner

HEMATOLOGY ANALYZERS AND METHODS OF OPERATION

CROSS REFERENCE TO RELATED APPLICATIONS

This application claims the benefit of U.S. Provisional Patent Application No. 62/578,239, filed on Oct. 27, 2017, entitled "METHODS OF OPERATING A HEMATOLOGY ANALYZER," which is hereby incorporated by reference in its entirety for all purposes.

FIELD

The present disclosure relates to using a control material to operate a hematology analyzer and hematology analyzers configured to use the control material. In particular, processing the control material may allow the hematology analyzer to monitor and calculate parameters associated with clinical conditions, including infections.

BACKGROUND

Quality control has long been a necessary and routine procedure in clinical hematology. Accuracy in the counting of various types of blood cells is dependent, in part, upon the use of adequate control materials and methods of using the control materials. With the numerous types of equipment for particle counting now available, quality control by the use of control materials is necessary, since the possibility of an instrument malfunctioning is ever present. Previous methods of maintaining a quality control program for automatic particle counting equipment has consisted of providing fresh human blood as a whole blood standard. However, this fresh blood is usable for only one day, therefore, various manufactured control materials which have longer product lifetime are desired.

Commonly used particles in a control product simulate or approximate the types of particles or cells that are intended to undergo analysis. Consequently, these particles have been frequently referred to as analog particles. The analog particles should be selected or designed so that they have certain characteristics that are similar to those of the particles or cells to be analyzed in the instruments. Exemplary characteristics and parameters include similarities in size, volume, surface characteristics, granularity properties, light scattering properties, and fluorescence properties. In addition to having a control material, the appropriate and relevant parameters for analysis still need to be understood. Because more characteristics and parameters are identified for diagnostics and for additional reasons, improved systems and methods for using control materials to ensure quality control are desired.

BRIEF SUMMARY

Instances of the present technology may allow for a hematology analyzer to monitor and calculate parameters associated with clinical conditions, including sepsis, systemic inflammatory response syndrome (SIRS), or an infection. Parameters associated with the clinical conditions may include the monocyte distribution width (e.g., standard deviation of the monocyte volume). Instances of the present technology may allow for using a control material that may be used repeatedly for over 14 days. The control material may only need to be passed once in a single container through an instrument to monitor the parameters.

In a first aspect, instances of the present technology may include a method for operating a hematology analyzer. The method may include passing a control material through a hematology analyzer. The control material may include a first cell population and a second cell population. The method may also include determining, using the hematology analyzer, a first cell population volume measurement. The method may further include determining, using the hematology analyzer, a second cell population volume measurement. From the first cell population volume measurement, a first value of a first cell population distribution width may be calculated. From the second cell population volume measurement, a second value of a second cell population distribution width may be calculated. In addition, the method may include comparing the first value to a first reference range. The method may also include comparing the second value to a second reference range. Furthermore, the method may include classifying an operational status of the hematology analyzer based on the comparison of the first value to the first reference range and based on the comparison of the second value to the second reference range.

In a second aspect, instances of the present technology may include an automated system for evaluating an infection status associated with a blood sample obtained from an individual. The system may include a transducer for obtaining current data for a control material as the control material passes through an aperture. The control material may include a first cell population and a second cell population. The system may include a processor. The system may also include a non-transitory computer readable medium storing a plurality of instructions. When executed by the processor, the plurality of instructions may cause the system to obtain current data for the control material. The system may further be caused to determine a first cell population volume measurement, using the current data. The system may also be caused to determine a second cell population volume measurement using the current data. The instructions may also cause the system to calculate a first value of a first cell population distribution width from the first cell population volume measurement. The instructions may further cause the system to calculate a second value of a second cell population distribution width from the second cell population volume measurement. The system may further be caused to compare the first value to a first reference range. The system may be caused to compare the second value to a second reference range. Furthermore, the instructions may further cause the system to classify an operational status of the automated system based on the comparison of the first value to the first reference range and based on the comparison of the second value to the second reference range.

A better understanding of the nature and advantages of embodiments of the present invention may be gained with reference to the following detailed description and the accompanying drawings.

DETAILED DESCRIPTION

Sepsis is an uncontrolled systemic inflammatory response to infection that may rapidly progress to a life-threatening condition that can lead to shock and organ failure (i.e., septic shock and severe sepsis) if not treated immediately. A patient admitted to a medical facility may show clinical features of systemic inflammation. A medical professional may then attempt to determine if the inflammation is caused by an infection, leading to a diagnosis of sepsis, or some other causes, leading to a diagnosis of systemic inflammatory response syndrome (SIRS). In some cases, a patient may have no obvious signs of systemic inflammation, which may mean that the patient may not be considered at risk for sepsis.

If undetected, sepsis may lead to severe sepsis or septic shock, which has a mortality rate of about 60%. A large fraction of hospital deaths are associated with sepsis. Diagnosing sepsis is challenging because of the lack of an accurate biomarker. Additionally, clinical criteria that may indicate sepsis, such as hypothermia, hyperthermia, tachycardia, tachypnea, may not distinguish sepsis from SIRS. These criteria may be associated with non-infectious etiologies that may be present in a hospital emergency room, including trauma, burns, pancreatitis, sickle cell crisis, and other inflammatory disorders. These similarities between sepsis and inflammation may make diagnosing sepsis challenging and time-consuming.

Methods to detect the presence of sepsis and/or SIRS have been described in U.S. Provisional Application No. 62/288, 091, filed Jan. 28, 2016; PCT Application No. PCT/US2017/ 014708, filed Jan. 24, 2017; and Park, D.-H., "Screening of sepsis using leukocyte cell population data from the Coulter automatic blood cell analyzer DxH800," *Int. Jnl. Lab. Hem.*, 2011, 33, 391-399, the contents of all of which are incorporated by reference for all purposes. These methods may include the use of a measure of the standard deviation of monocyte volume, which is a measure of the monocyte distribution width (MDW). The MDW may be used to determine the infection status of a patient with high specificity and sensitivity.

Figure 1:
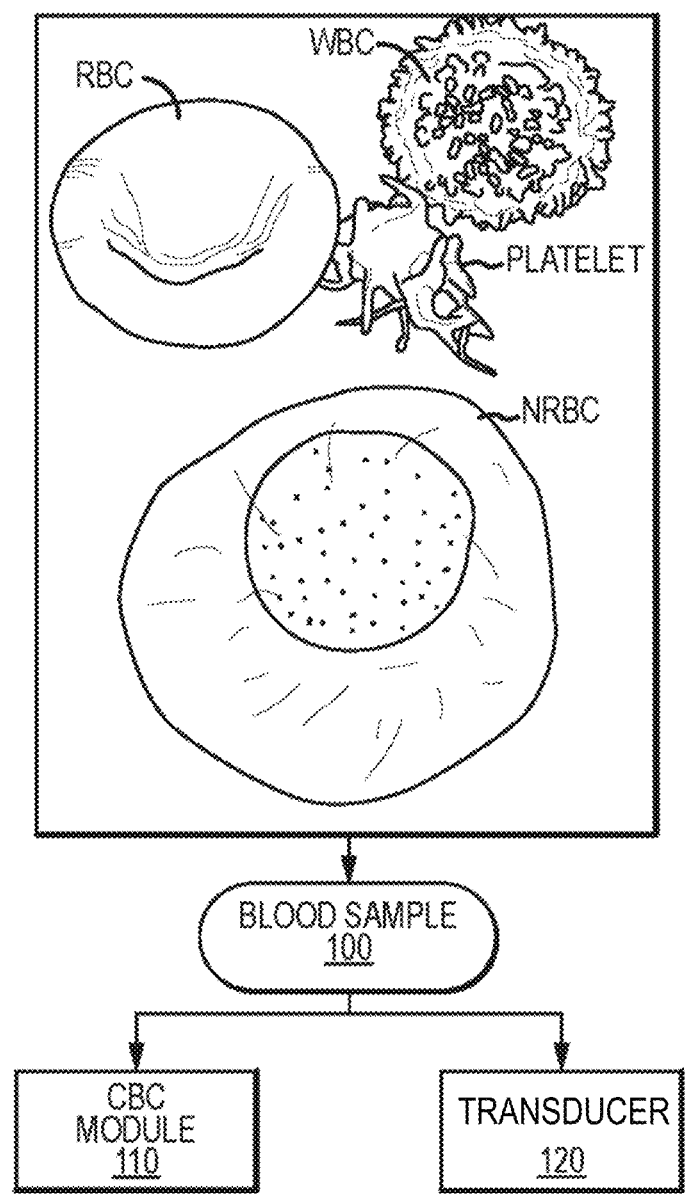
FIG. 1 illustrates aspects of blood cell analysis according to instances of the present invention.

FIG. 1 illustrates aspects of an example analysis technique. As shown here, and as discussed elsewhere herein, a whole blood sample 100 may include cells such as platelets, white blood cells (WBCs), and red blood cells (RBCs), including nucleated red blood cells (NRBCs). Various RBC, WBC, and NRBC parameters, obtained from channel processing mechanisms such as a complete blood count (CBC) module 110 or transducer 120 (VCSn module), can be evaluated to assess the infection status of an individual. The transducer may obtain current data for blood samples as the sample passes through an aperture. The aperture may be part of a flow cell.

A parameter of interest for infection status evaluation is the monocyte distribution width. MDW may vary over a range of values for healthy individuals and for individuals with an infection. For example, the MDW for an individual with sepsis may be higher than for a healthy individual. A cutoff to determine whether the MDW is statistically different from the MDW for a healthy individual may be used to evaluate the infection status of an individual. The cutoff may be determined based on a desired sensitivity or specificity for evaluating the infection status or for calculating a parameter used to evaluate the infection status. In order to reliably measure the MDW range that can be used for clinical determinations, an instrument may need to be verified to be operational over a range of MDW values greater than or equal to the ranges of MDW between healthy and non-healthy individuals.

A control material or control product may be analyzed by a hematology analyzer to verify that the hematology analyzer is operational over a desired range. Control products have been discussed in U.S. Pat. No. 7,393,688 (issued Jul. 1, 2008), U.S. Pat. No. 7,285,417 (issued Oct. 23, 2007), U.S. Pat. No. 7,135,341 (issued Nov. 14, 2006), U.S. Pat. No. 7,109,036 (issued Sep. 19, 2006) and U.S. Pat. No. 5,529,933 (issued Jun. 25, 1996), the contents of all of which are incorporated herein by reference for all purposes. Control material may include blood cells and analogs to be analyzed and compared to known reference ranges. Control materials may be introduced to CBC module 110 or transducer 120 in place of blood sample 100.

Without the control material and methods described herein, the hematology analyzer may not be able (technically or legally) to determine whether the hematology analyzer is operating correctly over a given range, particularly a range for monocyte distribution width for the detection of sepsis or other infection. As a result, the hematology analyzer is an improved analyzer. With confirmation that the hematology analyzer is functioning properly, the hematology analyzer may be able to avoid duplicate sample runs, additional sample withdrawals from a patient, and/or discarded runs when the hematology analyzer is not operational. The methods may also correct the infection status of a patient if the hematology analyzer is found to be non-operational near the time a blood sample of the patient is tested. The control material and methods provide an improvement to the technical fields of hematology analysis, biology, and medicine. Moreover, a computer programmed to perform the methods described herein may not be a generic computer but a specialized computer of performing hematology analysis.

The control material may include a stabilized, platelet-sized component, and fixed animal erythrocytes to simulate leukocytes and nucleated red blood cells. Any blood cells suitable for simulating human blood cells may be used. Blood cells include various nucleated animal red blood cells and mammalian white blood cells. Blood cells may include human, primate, mammalian, avian, fish, ungulate blood cells. For example, alligator, shark, salmon, goat, sheep, horse, ostrich, emu, or goose red blood cells, and mammalian lymphocytes from whole blood or grown in vitro by a cell line can be used. In addition, synthetic particles may be used to simulate blood cells. Synthetic particles may be spherical particles having optical particles simulating optical properties of blood cells. Synthetic particles may be made of polystyrene or carboxylated polystyrene. Synthetic particles are described in U.S. Pat. No. 7,176,031 (issued Feb. 13, 2007), which is incorporated herein by reference for all purposes. The control material may include cells attached to a coating or polymer (e.g., a biopolymer described in U.S. Pat. No. 7,195,919, which is incorporated herein by reference for all purposes).

The control material may include three different levels of cells volumes, which may include one normal level and two abnormal levels. For example, the control material may include monocyte percentages ranging from 3% to 19%. The three levels may be in three separate tubes. Despite this range of monocyte percentages, the control material may not include a monocyte distribution width range that covers the range needed to identify a clinical condition in a patient. A high monocyte distribution width (i.e., a high dispersion), and a low monocyte distribution width (i.e., a low dispersion) may be needed. The high monocyte distribution width may be satisfied with monocytes from the processed alligator red blood cells. The origin of the cell population for the distribution width may not affect the accuracy or precision of the hematology analyzer. As a result, for the low monocyte distribution width, the lymphocyte distribution width from Goose fixed red blood cells may be used. Cells used for the high monocyte distribution width and the low monocyte distribution may include or exclude any type of blood cell from any animal described herein. Furthermore, the cells may include or exclude any synthetic component described herein.

Figure 2:
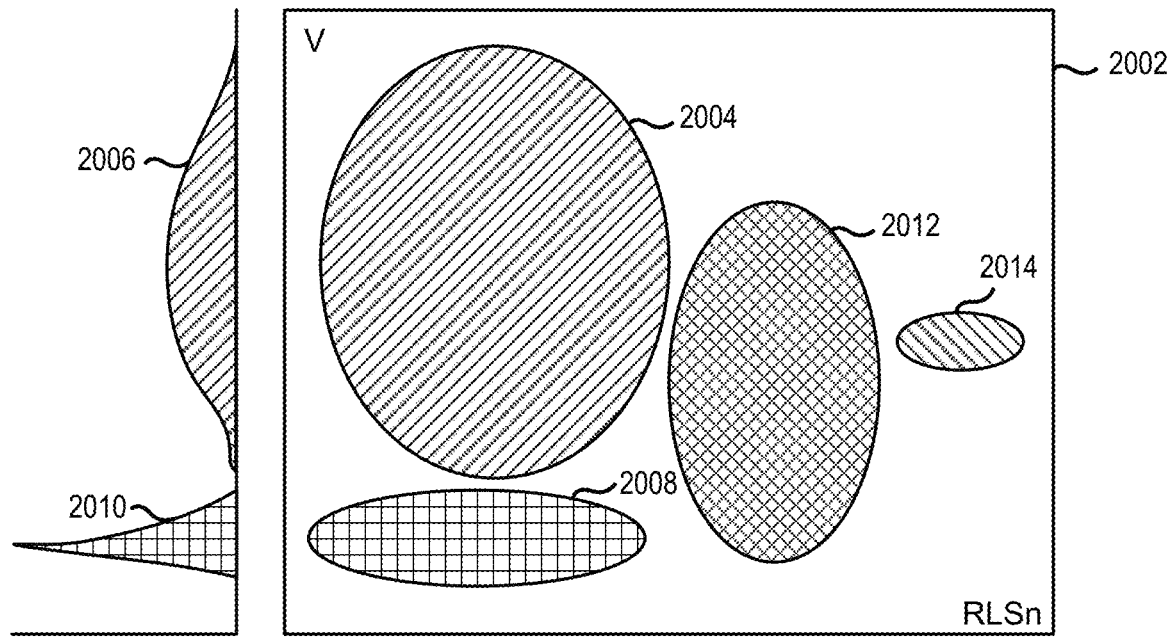
FIG. 2 illustrates a plot of parameters of different cells in a control material according to instances of the present invention.

FIG. 2 shows an example of how different cells may be used in a control material. Plot 2002 is a graph of cell size (volume) on the y-axis and light scatter on the x-axis. Region 2004 may include a distribution of analog cells that resemble monocytes. For example, the monocytes may be simulated from processed alligator red blood cells. The distribution of the simulated monocytes may be shown as distribution 2006, which is plotted with volume on the y-axis and amount on the x-axis. Distribution 2006 may have a distribution width (e.g., a standard deviation, a percentile difference from the 50% percentile) that may be high enough for the desired range. In other words, the distribution width may be larger than a distribution width used for determining a clinical cutoff. However, the simulated monocytes in the control material may all be similar to distribution 2006 and may not have a distribution width on the low end of the desired range.

Region 2008 may include a distribution of cells that resemble lymphocytes. For example, the lymphocytes may be simulated from Goose fixed red blood cells. Distribution 2010 may be the distribution of cells from region 2008. The distribution width of distribution 2010 may be on the low end of the desired range. For example, the distribution width of distribution 2010 may be lower than a clinical cutoff that may be used for evaluating an infection status. Distribution 2006 and distribution 2010 may therefore verify that a hematology analyzer can accurately operate over a sufficient range that may cover the clinical cutoff. The range may include the clinical cutoff, a MDW indicative of a healthy individual, and an MDW indicative of a patient with an infection.

A control material may include cells from region 2004 and cells from region 2008 to verify the desired operating range of the hematology analyzer. By analyzing the control material and verifying the distribution widths of distribution 2006 and distribution 2010 against previously measured or known distribution widths, the hematology analyzer may be dispositioned as operational or non-operational. While FIG. 2 shows the distributions of region 2004 and region 2008 being used, distribution of other regions with other cells may also be used. For example, region 2012 may generate a distribution with a high distribution width, and region 2014 may generate a distribution with a low distribution width. These regions may include different types of cells.

I. Methods

Figure 3:
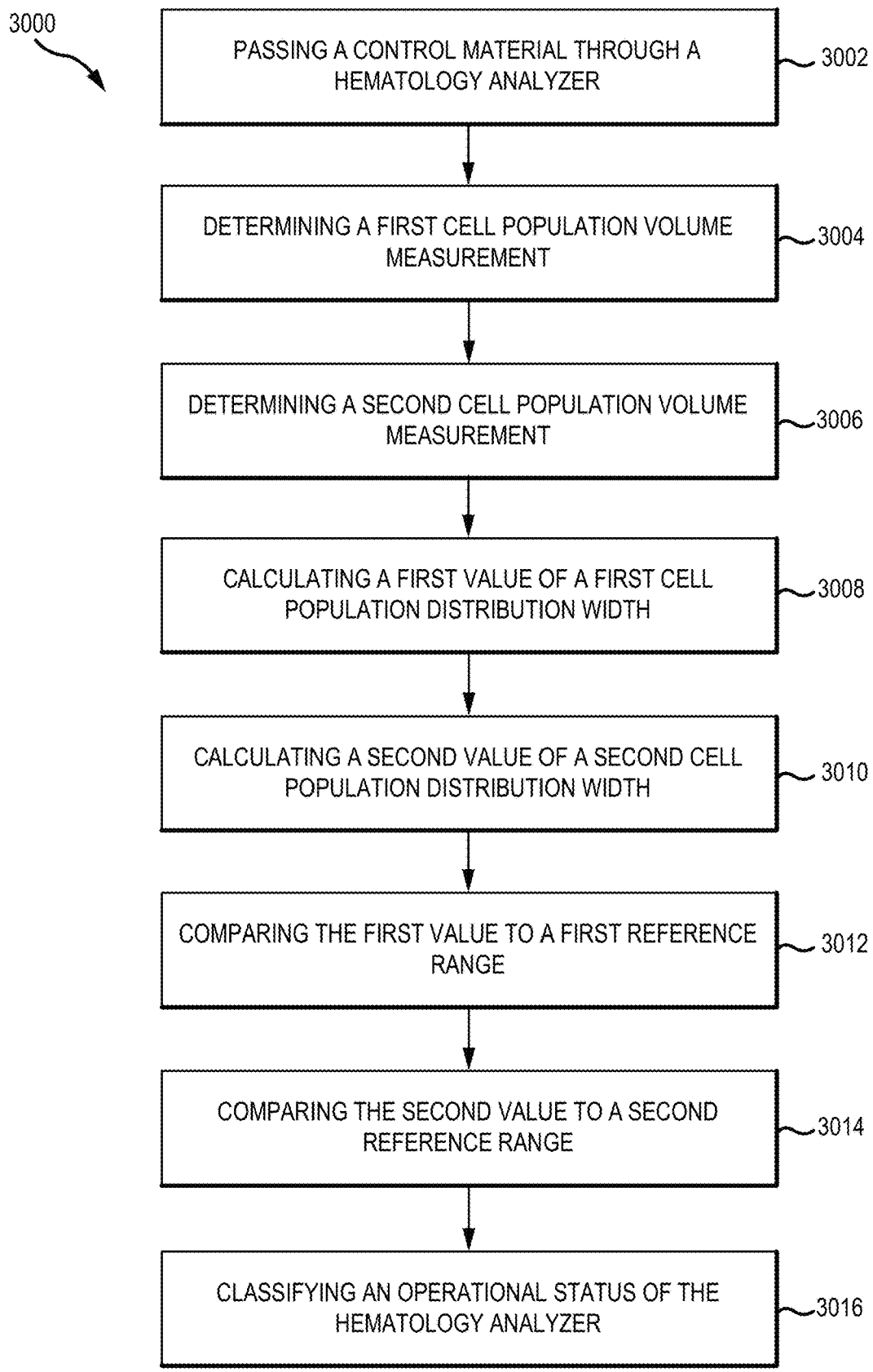
FIG. 3 shows a method of operating a hematology analyzer according to instances of the present invention.

FIG. 3 shows a method 3000 for operating a hematology analyzer. Method 3000 may include passing a control material through a hematology analyzer (block 3002). The control material may be aspirated into the hematology analyzer. The control material can be passed through a flow cell in a transducer system such that sample constituents (e.g. blood cells) pass through a cell interrogation zone in a one by one fashion.

The control material may include a first cell population and a second cell population. In some instances, the first cell population or the second cell population may simulate a cell type selected from the group consisting of monocytes, neutrophils, lymphocytes, eosinophils, basophils, and mixtures thereof. The first cell population or the second cell population may exclude any cell type or mixtures of cell types described herein. The first cell population may simulate properties of human monocytes. The first cell population may include processed alligator red blood cells. The second cell population may simulate human lymphocytes. The second cell population may include Goose fixed red blood cells. The control material may further include or exclude any cells or synthetic components described herein. The control material may be any control material or control product described herein.

The control material may be characterized before passing the control material through the hematology analyzer. Characterizing the control material may include determining certain properties, such as certain cell population parameters, of the control material. Characterizing the properties may involve formulating the control material using a known and controlled source of cells and/or cell analogs to produce a control material with known cell population parameters. Alternately, or in addition, to formulating the control material to have known cell population parameters, the properties of a control material may be characterized by analyzing the control material in one or more analyzers of known operational status. The characterization analyzers may be of the same or different type as the analyzers with which the control material will ultimately be used to determine operational status. The characterization may involve analyzing the control material using a single analyzer known to be operational. The characterization may involve analyzing the control material using two or more analyzers to confirm that the results across a plurality of analyzers are consistent.

Before passing the control material through the hematology analyzer, the first cell population may be characterized by a value of the first cell population distribution width greater than a value of a monocyte distribution width from a healthy individual. In this case, greater may mean statistically greater. The value of the first cell population distribution width may be greater than the cell population distribution width used for determining a clinical cutoff value, which may be determined as described herein. The clinical cutoff value may be an indication of a clinical condition, such as an infection, sepsis, SIRS, or any condition described herein. The value of the first cell population distribution width may indicate a clinical condition. In these and other instances, the value of the first cell population distribution width may be greater than an expected range of the monocyte distribution width. The expected range may be calculated based on empirical data. For example, the expected range may be 1, 2, or 3 standard deviations from a mean average of experimentally derived measurements. In some instances, the expected range may be a certain percentile range of experimental data.

Also before passing the control material through the hematology analyzer, the second cell population may be characterized by a value of the second cell population distribution width lower than a value of a monocyte distribution width from an individual with an infection, including any infection described herein. In this case, lower may mean statistically lower. The value of the second cell population distribution width may be lower than the cell population distribution width used for determining a clinical cutoff value. The value of the second cell population distribution width may be lower than an MDW indicative of a healthy individual. In these and other instances, the value of the second cell population distribution width may be lower than the expected range of the monocyte distribution width, which may be determined empirically.

Method 3000 may also include determining, using the hematology analyzer, a first cell population volume measurement (block 3004). Determining the first cell population volume measurement may include measuring direct current (DC) impedance or radio frequency (RF) conductivity. Determining the first cell population volume measurement may include measuring an optical parameter. The optical parameter may be a light scatter parameter selected from a group consisting of upper median angle light scatter (UMALS), lower median angle light scatter (LMALS), median angle light scatter (MALS), lower angle light scatter (LALS). The optical parameter may be axial light loss (ALL or AL2). Determining the first cell population volume measurement may include irradiating the control material by a light source, such as a laser. The first cell population volume measurement may be a cell volume, including, for example, the monocyte volume.

Method 3000 may further include determining, using the hematology analyzer, a second cell population volume measurement (block 3006). The second cell population volume measurement may be determined in any way the first cell population volume is determined. The second cell population volume measurement may be a cell volume, including, for example, the lymphocyte volume.

Method 3000 may include calculating a first value of a first cell population distribution width from the first cell population volume measurement (block 3008), The first cell population distribution width may include a monocyte distribution width.

Method 3000 may include calculating a second value of a second cell population distribution width from the second cell population volume measurement (block 3010). Calculating at least one of the first value or the second value may include calculating the standard deviation, the coefficient of variation, a percentile range, or a dispersion measurement of the corresponding cell population volume measurement.

Method 3000 may include comparing the first value to a first reference range (block 3012). A previously characterized value of the first cell distribution width may be within the first reference range. The comparison may include determining whether the first value is within the first reference range. The first reference range may be predetermined. In some instances, determining the first reference range may include previously calculating the first cell distribution width. Determining the first reference range may also include determining the variability in calculating the first cell distribution width. The determination of the variability may include using statistical analysis. In these or other instances, the first reference range may be based on previously calculated first values and variability for the control material and the given hematology analyzer. The first reference range may be the previously calculated first cell distribution width plus or minus some uncertainty interval.

The first reference range may be greater than or equal to a value of a monocyte distribution width from an individual with an infection, wherein the infection is any infection described herein. The first reference range may be greater than or equal to any range for a cutoff value used in evaluating the sepsis status of an individual, including cutoff value ranges described in U.S. 62/660,795, filed Apr. 20, 2018, the contents of which are incorporated herein by reference for all purposes. The first reference range may be greater than or equal to ranges from 19 to 20, from 19.5 to 20.5, from 19 to 21, from 18 to 22, from 20 to 25, from 25 to 30, from 30 to 35, or greater than 35.

Method 3000 may also include comparing the second value to a second reference range (block 3014). A previously characterized value of the second cell distribution width may be within the second reference range. The comparison may include determining whether the second value is within the second reference range. In some instances, the second reference range may include previously calculating the second cell distribution width. Determining the second reference range may also include determining the variability in calculating the second cell distribution width. The determination of the variability may include using statistical analysis. In these or other instances, the second reference range may be based on previously calculated second values and variability for the control material and the given hematology analyzer. The first reference range may be the previously calculated second cell distribution width plus or minus some uncertainty interval.

The second reference range may be less than or equal to a value of a monocyte distribution width from a healthy individual. The first reference range may be less than or equal to any range for a cutoff value used in evaluating the sepsis status of an individual. The first reference range may be less than or equal to ranges from 17 to 18, from 16 to 17, from 15 to 16, from 10 to 15, from 5 to 10, or less than 5.

Furthermore, method 3000 may include classifying an operational status of the hematology analyzer based on the comparison of the first value to the first reference range and based on the comparison of the second value to the second reference range (block 3016). Classifying the hematology analyzer as operational may be upon determining that the first value is within the first reference range and determining that the second value is within the second reference range. Classifying the hematology analyzer as not operational may be upon at least one of determining that the first value is outside the first reference range or determining that the second value is outside the second reference range. One of technical skill in the art would recognize that determining whether a value in the range may be equivalent to determining whether a value is statistically equivalent to another value.

The operational status of the hematology analyzer may be further analyzed by any suitable statistical process control technique. The method may include communicating the operational status of the hematology analyzer to a user. Communicating the operational status may be by a message on a monitor, a light indicator, a sound indicator, or other suitable electronic communication. The method may include prompting the user to acknowledge the communication of the operational status.

A cellular analysis system may be configured to classify the operational status and to perform determination, calculation, and comparison operations before classification. As discussed elsewhere herein, in some instances at least a portion of the operations can be performed using one or more software modules executable by one or more processors, one or more hardware modules, or any combination thereof. Processors or other computer or module systems may be configured to receive as an input values for the various measurements or parameters and automatically output the classified operational status. In some instances, one or more of the software modules, processors, and/or hardware modules may be included as a component of a hematology system that is equipped to obtain multiple light angle detection parameters, such as Beckman Coulter's UniCel® DxH™ Cellular Analysis System. In some instances, one or more of the software modules, processors, and/or hardware modules may be included as a component of a stand-alone computer that is in operative communication or connectivity with a hematology system that is equipped to obtain multiple light angle detection parameters, such as Beckman Coulter's UniCel® DxH™ System. In some instances, at least a portion of the classification can be performed by one or more of the software modules, processors, and/or hardware modules that receive data from a hematology system that is equipped to obtain multiple light angle detection parameters, such as Beckman Coulter's UniCel® DxH™ System remotely via the internet or any other over wired and/or wireless communication network. Relatedly, each of the devices or modules according to embodiments of the present invention can include one or more software modules on a computer readable medium that is processed by a processor, or hardware modules, or any combination thereof.

Method 3000 may further include classifying the hematology analyzer as operational. After classifying the hematology analyzer as operational, method 3000 may also include passing a blood sample from a patient through the hematology analyzer. Method 3000 may include determining, using the hematology analyzer, a monocyte distribution width in the blood sample. Method 3000 may include evaluating an infection status associated with the blood sample based on the monocyte distribution width. Evaluating the infection status may include determining an infection is present. Evaluating the infection status may include considering other parameters in the blood sample besides MDW as well as considering symptoms in the patient associated with the blood sample.

If an infection is determined to be present, method 3000 may further include treating the patient for the infection. Treatment may include closer monitoring, hospital admission, aggressive IV fluids, repeated blood cultures, and prioritized diagnoses. The treatment may be earlier than with other conventional methods because the infection is determined to be present earlier than can be determined with conventional methods. As a result, the patient's prognosis can be improved and the patient's risk of death can be decreased.

After classifying the operational status as operational, method 3000 may include passing the control material again through the hematology analyzer within 8 hours, 16 hours, or 24 hours of passing the control material through the hematology analyzer. The control material may be passed through the hematology analyzer at repeated intervals over the course of 14 to 21 days, including 14, 15, 16, 17, 18, 19, 20, or 21 days. The control material may be passed through the hematology analyzer 14 to 21 times, including 14, 15, 16, 17, 18, 19, 20, or 21 times. The number of passes through the hematology analyzer may or may not be the same as the number of days. In some instances, passing the control material through the hematology analyzer may be before a blood sample is passed through.

Method 3000 may include classifying the operational status as not operational, and based on the classification, preventing an input of a blood sample into the hematology analyzer after the control material. Preventing the input of a blood sample may include reducing or shutting off power to certain components of the hematology analyzer. The operational status of the hematology analyzer may be communicated electronically to a field service engineer.

After a hematology analyzer has been classified as not operational, method 3000 may include passing the control material through the hematology analyzer again in order to confirm or reject the classification status. For example, the classification status may be changed to operational if two consecutive analyses of the control material result in the resulting first values being greater than the first reference range and the resulting second values being less than the second reference range. The classification of the hematology analyzer as not operational may be automatically communicated to a field service engineer, who may be trained to calibrate or repair the hematology analyzer.

If the hematology analyzer has been classified as not operational, diagnostics, calibration, and/or repairs may be performed on the hematology analyzer. After the diagnostics, calibration, and/or repairs and as part of bringing the hematology analyzer back online, the method of classifying the operational status of the hematology analyzer may be repeated before analyzing a non-control, blood sample. In addition, if the hematology analyzer has been classified as not operational, the blood samples that passed through the hematology analyzer since the previous operational classification may be identified. The blood samples may be retested in the hematology analyzer after the hematology analyzer is classified as operational, or the blood samples may be tested in a different, operational hematology analyzer. The infection status of the patients, from which the blood samples are taken, may be updated to reflect an unknown result from the hematology analyzer. In some cases, patients classified as septic may be reclassified as normal, and in some cases, patients classified as normal may be reclassified as septic. False positives and false negatives may be reduced through this identification and as-needed reclassification. In some instances, new blood samples may be obtained from the patients for testing in an operational hematology analyzer.

II. Systems

Instances of the present technology may include an automated system for evaluating an infection status associated with a blood sample obtained from an individual. The system may include a transducer for obtaining current data for a control material as the control material passes through an aperture. As used herein, "current" refers to electrical current or RF conductivity, rather than data that is up-to-date or recent. The control material may include a first cell population and a second cell population. The system may include a processor. The system may also include a non-transitory computer readable medium storing a plurality of instructions. When executed by the processor, the plurality of instructions may cause the system to obtain current data for the control material. The system may further be caused to determine a first cell population volume measurement, using the current data. The system may also be caused to determine a second cell population volume measurement using the current data. The instructions may also cause the system to calculate a first value of a first cell population distribution width from the first cell population volume measurement. The instructions may further cause the system to calculate a second value of a second cell population distribution width from the second cell population volume measurement. The system may further be caused to compare the first value to a first reference range. The system may be caused to compare the second value to a second reference range. Furthermore, the instructions may further cause the system to classify an operational status of the automated system based on the comparison of the first value to the first reference range and based on the comparison of the second value to the second reference range.

The automated system may further include a scanner. The plurality of instructions may further cause the system to identify, using the scanner, a container with the control material as containing the control material. The scanner may be a barcode scanner, a QR code scanner, an RFID scanner, or any suitable scanner.

The plurality of instructions may cause the system to perform any method described herein. The automated system may include a hematology analyzer. Additional description of systems and components are described below.

Figure 4:
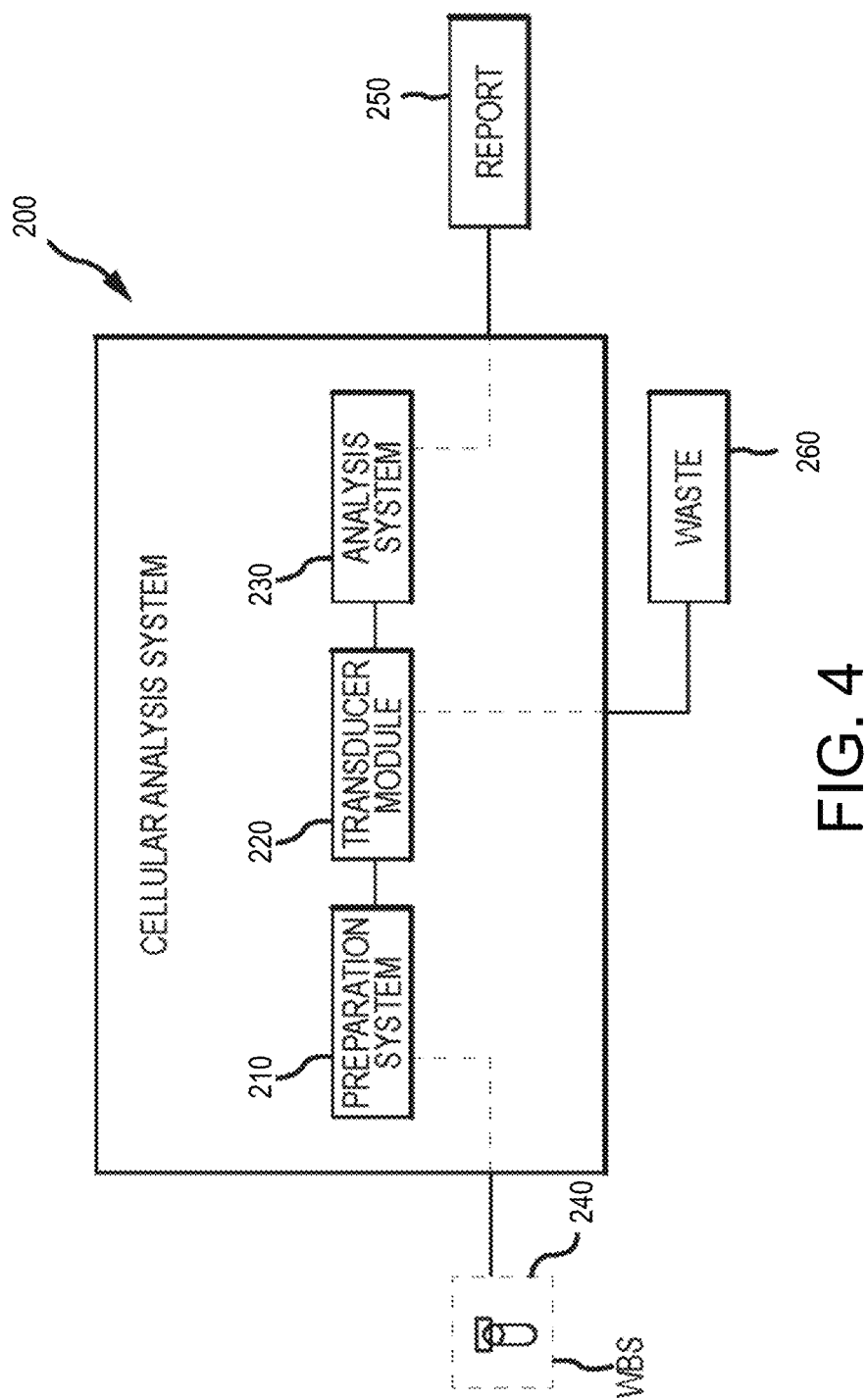
FIG. 4 schematically depicts aspects of a cellular analysis system according to instances of the present invention.

FIG. 4 schematically depicts a cellular analysis system 200. As shown here, system 200 includes a preparation system 210, a transducer module 220, and an analysis system 230. While system 200 is herein described at a very high level, with reference to the three core system blocks (210, 220, and 230), one of skill in the art would readily understand that system 200 includes many other system components such as central control processor(s), display system(s), fluidic system(s), temperature control system(s), user-safety control system(s), and the like. In operation, a whole blood sample (WBS) 240 can be presented to the system 200 for analysis. Although not shown in FIG. 4, control material may be presented to system 200 in place of WBS. In some instances, WBS 240 is aspirated into system 200. Exemplary aspiration techniques are known to the skilled artisan. After aspiration, WBS 240 can be delivered to a preparation system 210. Preparation system 210 receives WBS 240 and can perform operations involved with preparing WBS 240 for further measurement and analysis. For example, preparation system 210 may separate WBS 240 into predefined aliquots for presentation to transducer module 220. Preparation system 210 may also include mixing chambers so that appropriate reagents may be added to the aliquots. For example, where an aliquot is to be tested for differentiation of white blood cell subset populations, a lysing reagent (e.g. ERYTHROLYSE, a red blood cell lysing buffer) may be added to the aliquot to break up and remove the RBCs. Preparation system 210 may also include temperature control components to control the temperature of the reagents and/or mixing chambers. Appropriate temperature controls can improve the consistency of the operations of preparation system 210.

In some instances, predefined aliquots can be transferred from preparation system 210 to transducer module 220. As described in further detail below, transducer module 220 can perform direct current (DC) impedance, radiofrequency (RF) conductivity, light transmission, and/or light scatter measurements of cells from the WBS passing individually therethrough. Measured DC impedance, RF conductivity, and light propagation (e.g. light transmission, light scatter) parameters can be provided or transmitted to analysis system 230 for data processing. In some instances, analysis system 230 may include computer processing features and/or one or more modules or components such as those described herein with reference to the system depicted in FIG. 7 and described further below, which can evaluate the measured parameters, identify and enumerate the WBS constituents, and correlate a subset of data characterizing elements of the WBS with an infection status. As shown here, cellular analysis system 200 may generate or output a report 250 containing the evaluated infection status and/or a prescribed treatment regimen for the individual. In some instances, excess biological sample from transducer module 220 can be directed to an external (or alternatively internal) waste system 260.

Figure 5:
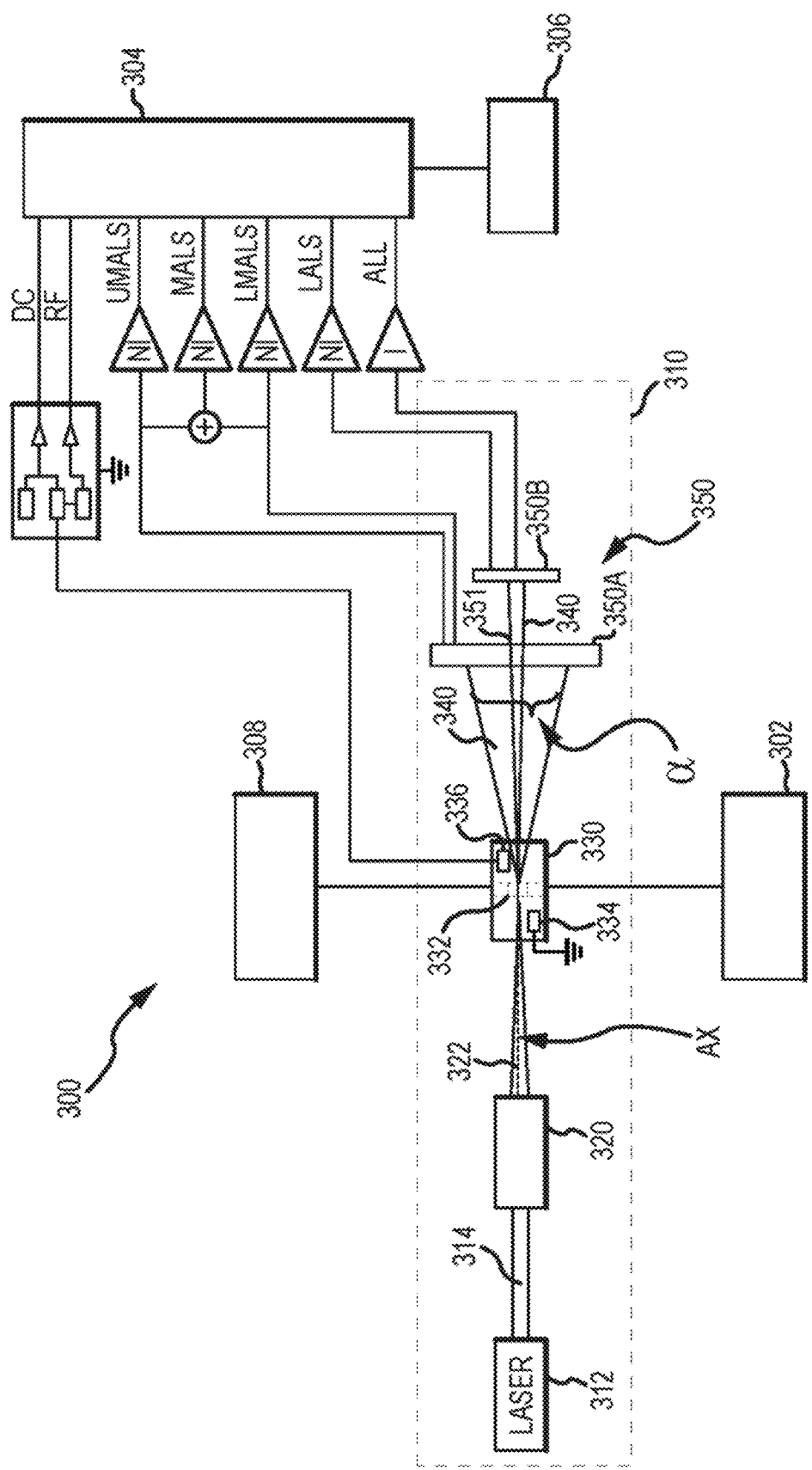
FIG. 5 provides a system block diagram illustrating aspects of a cellular analysis system according to instances of the present invention.

FIG. 5 illustrates in more detail a transducer module and associated components in more detail. As shown here, system 300 includes a transducer module 310 having a light or irradiation source such as a laser 312 emitting a beam 314. The laser 312 can be, for example, a 635 nm, 5 mW, solid-state laser. In some instances, system 300 may include a focus-alignment system 320 that adjusts beam 314 such that a resulting beam 322 is focused and positioned at a cell interrogation zone 332 of a flow cell 330. In some instances, flow cell 330 receives a sample aliquot from a preparation system 302. As described elsewhere herein, various fluidic mechanisms and techniques can be employed for hydrodynamic focusing of the sample aliquot within flow cell 330.

In some instances, the aliquot generally flows through the cell interrogation zone 332 such that its constituents pass through the cell interrogation zone 332 one at a time. In some cases, a system 300 may include a cell interrogation zone or other feature of a transducer module or blood analysis instrument such as those described in U.S. Pat. Nos. 5,125,737; 6,228,652; 7,390,662; 8,094,299; and 8,189,187, the contents of which are incorporated herein by references. For example, a cell interrogation zone 332 may be defined by a square transverse cross-section measuring approximately 50×50 microns, and having a length (measured in the direction of flow) of approximately 65 microns. Flow cell 330 may include an electrode assembly having first and second electrodes 334, 336 for performing DC impedance and RF conductivity measurements of the cells passing through cell interrogation zone 332. Signals from electrodes 334, 336 can be transmitted to analysis system 304. The electrode assembly can analyze volume and conductivity characteristics of the cells using low-frequency current and high-frequency current, respectively. For example, low-frequency DC impedance measurements can be used to analyze the volume of each individual cell passing through the cell interrogation zone. Relatedly, high-frequency RF current measurements can be used to determine the conductivity of cells passing through the cell interrogation zone. Because cell walls act as conductors to high frequency current, the high frequency current can be used to detect differences in the insulating properties of the cell components, as the current passes through the cell walls and through each cell interior. High frequency current can be used to characterize nuclear and granular constituents and the chemical composition of the cell interior.

Incoming beam 322 travels along beam axis AX and irradiates the cells passing through cell interrogation zone 332, resulting in light propagation within an angular range α (e.g. scatter, transmission) emanating from the zone 332. Exemplary systems are equipped with sensor assemblies that can detect light within three, four, five, or more angular ranges within the angular range α, including light associated with an extinction or axial light loss measure as described elsewhere herein. As shown here, light propagation 340 can be detected by a light detection assembly 350, optionally having a light scatter detector unit 350A and a light scatter and transmission detector unit 350B. In some instances, light scatter detector unit 350A includes a photoactive region or sensor zone for detecting and measuring upper median angle light scatter (UMALS), for example light that is scattered or otherwise propagated at angles relative to a light beam axis within a range from about 20 to about 42 degrees. In some instances, UMALS corresponds to light propagated within an angular range from between about 20 to about 43 degrees, relative to the incoming beam axis which irradiates cells flowing through the interrogation zone. Light scatter detector unit 350A may also include a photoactive region or sensor zone for detecting and measuring lower median angle light scatter (LMALS), for example light that is scattered or otherwise propagated at angles relative to a light beam axis within a range from about 10 to about 20 degrees. In some instances, LMALS corresponds to light propagated within an angular range from between about 9 to about 19 degrees, relative to the incoming beam axis which irradiates cells flowing through the interrogation zone.

A combination of UMALS and LMALS is defined as median angle light scatter (MALS), which is light scatter or propagation at angles between about 9 degrees and about 43 degrees relative to the incoming beam axis which irradiates cells flowing through the interrogation zone.

As shown in FIG. 5, the light scatter detector unit 350A may include an opening 351 that allows low angle light scatter or propagation 340 to pass beyond light scatter detector unit 350A and thereby reach and be detected by light scatter and transmission detector unit 350B. According to some embodiments, light scatter and transmission detector unit 350B may include a photoactive region or sensor zone for detecting and measuring lower angle light scatter (LALS), for example light that is scattered or propagated at angles relative to an irradiating light beam axis of about 5.1 degrees. In some instances, LALS corresponds to light propagated at an angle of less than about 9 degrees, relative to the incoming beam axis which irradiates cells flowing through the interrogation zone. In some instances, LALS corresponds to light propagated at an angle of less than about 10 degrees, relative to the incoming beam axis which irradiates cells flowing through the interrogation zone. In some instances, LALS corresponds to light propagated at an angle of about 1.9 degrees±0.5 degrees, relative to the incoming beam axis which irradiates cells flowing through the interrogation zone. In some instances, LALS corresponds to light propagated at an angle of about 3.0 degrees±0.5 degrees, relative to the incoming beam axis which irradiates cells flowing through the interrogation zone. In some instances, LALS corresponds to light propagated at an angle of about 3.7 degrees±0.5 degrees, relative to the incoming beam axis which irradiates cells flowing through the interrogation zone. In some instances, LALS corresponds to light propagated at an angle of about 5.1 degrees±0.5 degrees, relative to the incoming beam axis which irradiates cells flowing through the interrogation zone. In some instances, LALS corresponds to light propagated at an angle of about 7.0 degrees±0.5 degrees, relative to the incoming beam axis which irradiates cells flowing through the interrogation zone.

According to some embodiments, light scatter and transmission detector unit 350B may include a photoactive region or sensor zone for detecting and measuring light transmitted axially through the cells, or propagated from the irradiated cells, at an angle of 0 degrees relative to the incoming light beam axis. In some cases, the photoactive region or sensor zone may detect and measure light propagated axially from cells at angles of less than about 1 degree relative to the incoming light beam axis. In some cases, the photoactive region or sensor zone may detect and measure light propagated axially from cells at angles of less than about 0.5 degrees relative to the incoming light beam axis less. Such axially transmitted or propagated light measurements correspond to axial light loss (ALL or AL2). As noted in previously incorporated U.S. Pat. No. 7,390,662, when light interacts with a particle, some of the incident light changes direction through the scattering process (i.e. light scatter) and part of the light is absorbed by the particles. Both of these processes remove energy from the incident beam. When viewed along the incident axis of the beam, the light loss can be referred to as forward extinction or axial light loss. Axial light loss (ALL, also known as forward extinction) is generally the decrease in light energy due to a particle passing through a beam of incident light and being detected by a photo-detector. When the beam of incident light strikes a particle, the light is either scattered or absorbed, both of which remove energy from the incident light and the incident beam is attenuated. This attenuation is referred to as extinction. When viewed along the axis of the beam of incident light, it is referred to as axial light loss. Generally ALL signals are detected at an angle from about 0° to about 1° from the incident light. In a preferred embodiment of the present invention, ALL signals are collected in a circular area less than about 0.5° from the incident light axis. ALL signals are strongly influenced by the size of a cell or particle. Additional aspects of axial light loss measurement techniques are described in U.S. Pat. No. 7,390,662.

As such, the cellular analysis system 300 provides means for obtaining light propagation measurements, including light scatter and/or light transmission, for light emanating from the irradiated cells of the biological sample at any of a variety of angles or within any of a variety of angular ranges, including ALL and multiple distinct light scatter or propagation angles. For example, light detection assembly 350, including appropriate circuitry and/or processing units, provides a means for detecting and measuring UMALS, LMALS, LALS, MALS, and ALL.

Wires or other transmission or connectivity mechanisms can transmit signals from the electrode assembly (e.g. electrodes 334, 336), light scatter detector unit 350A, and/or light scatter and transmission detector unit 350B to analysis system 304 for processing. For example, measured DC impedance, RF conductivity, light transmission, and/or light scatter parameters can be provided or transmitted to analysis system 304 for data processing. In some instances, analysis system 304 may include computer processing features and/or one or more modules or components such as those described herein with reference to the system depicted in FIG. 7, which can evaluate the measured parameters, identify and enumerate biological sample constituents, and correlate a subset of data characterizing elements of the biological sample with an infection status of the individual. As shown here, cellular analysis system 300 may generate or output a report 306 containing the evaluated infection status and/or a prescribed treatment regimen for the individual. In some instances, excess biological sample from transducer module 310 can be directed to an external (or alternatively internal) waste system 308. In some instances, a cellular analysis system 300 may include one or more features of a transducer module or blood analysis instrument such as those described in previously incorporated U.S. Pat. Nos. 5,125,737; 6,228,652; 8,094,299; and 8,189,187.

Figure 6:
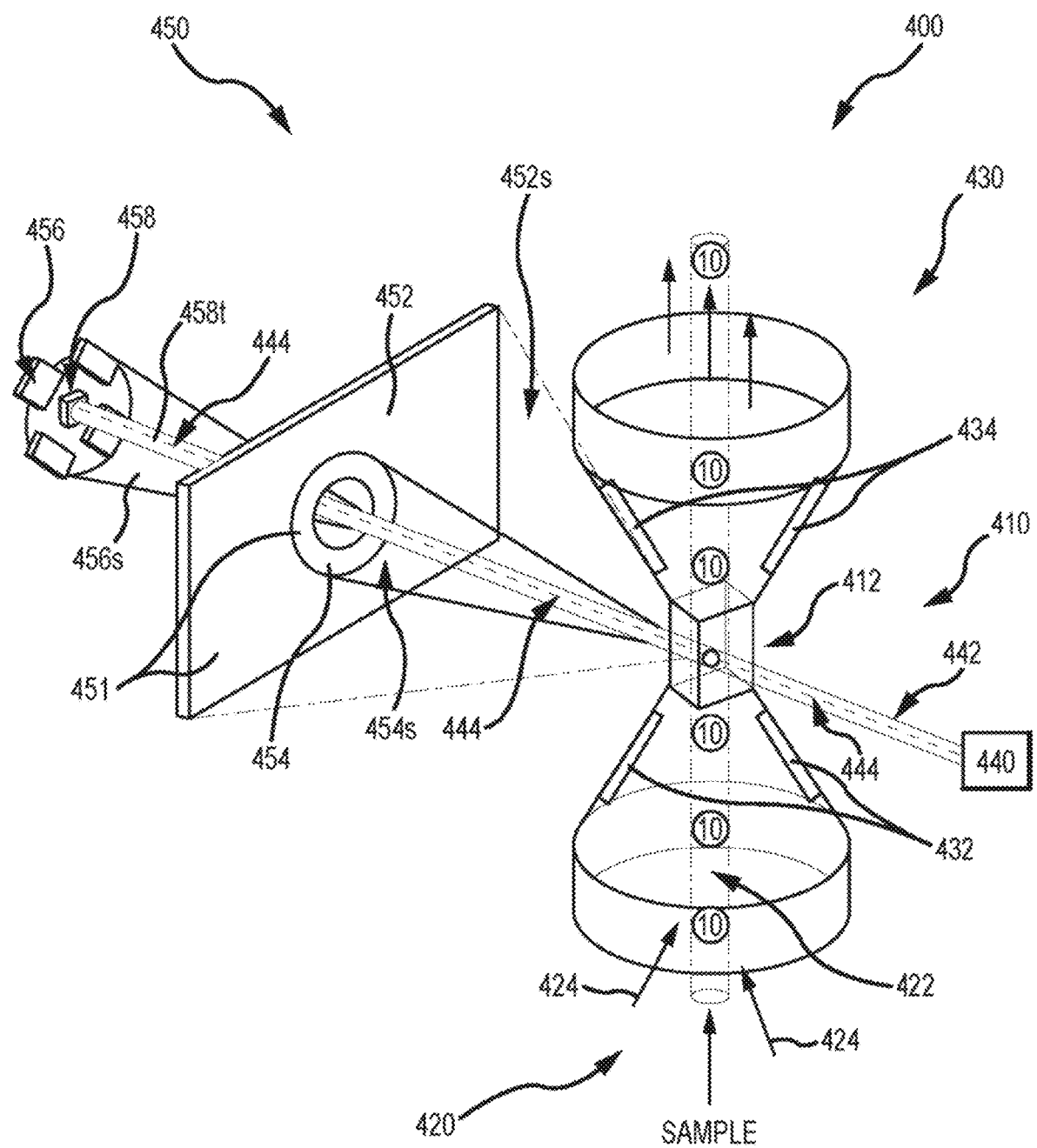
FIG. 6 illustrates aspects of an automated cellular analysis system for assessing a likelihood of infection in an individual according to instances of the present invention.

FIG. 6 illustrates aspects of an automated cellular analysis system for evaluating the infection status in an individual, according to embodiments of the present invention. In particular, the infection status can be evaluated based on a biological sample obtained from blood of the individual. As shown here, an analysis system or transducer 400 may include an optical element 410 having a cell interrogation zone 412. The transducer also provides a flow path 420, which delivers a hydrodynamically focused stream 422 of a biological sample toward the cell interrogation zone 412. For example, as the sample stream 422 is projected toward the cell interrogation zone 412, a volume of sheath fluid 424 can also enter the optical element 410 under pressure, so as to uniformly surround the sample stream 422 and cause the sample stream 422 to flow through the center of the cell interrogation zone 412, thus achieving hydrodynamic focusing of the sample stream. In this way, individual cells of the biological sample, passing through the cell interrogation zone one cell at a time, can be precisely analyzed.

Transducer module or system 400 also includes an electrode assembly 430 that measures direct current (DC) impedance and radiofrequency (RF) conductivity of cells of the biological sample passing individually through the cell interrogation zone 412. The electrode assembly 430 may include a first electrode mechanism 432 and a second electrode mechanism 434. As discussed elsewhere herein, low-frequency DC measurements can be used to analyze the volume of each individual cell passing through the cell interrogation zone. In some instances, the standard deviation of the volume of monocytes may be derived with low-frequency DC measurements. Relatedly, high-frequency RF current measurements can be used to determine the conductivity of cells passing through the cell interrogation zone. Such conductivity measurements can provide information regarding the internal cellular content of the cells. For example, high frequency RF current can be used to analyze nuclear and granular constituents, as well as the chemical composition of the cell interior, of individual cells passing through the cell interrogation zone.

The system 400 also includes a light source 440 oriented to direct a light beam 442 along a beam axis 444 to irradiate the cells 10 of the biological sample individually passing through the cell interrogation zone 412. Relatedly, the system 400 includes a light detection assembly 450 optically coupled with the cell interrogation zone, so as to measure light scattered by and transmitted through the irradiated cells 10 of the biological sample. The light detection assembly 450 can include a plurality of light sensor zones that detect and measure light propagating from the cell interrogation zone 412. In some instances, the light detection assembly detects light propagated from the cell interrogation zone at various angles or angular ranges relative to the irradiating beam axis. For example, light detection assembly 450 can detect and measure light that is scattered at various angles by the cells, as well as light that is transmitted axially by the cells along the beam axis. The light detection assembly 450 can include a first sensor zone 452 that measures a first scattered or propagated light 452s within a first range of angles relative to the light beam axis 444. The light detection assembly 450 can also include a second sensor zone 454 that measures a second scattered or propagated light 454s within a second range of angles relative to the light beam axis 444. As shown here, the second range of angles for scattered or propagated light 454s is different from the first range of angles for scattered or propagated light 452s. Further, the light detection assembly 450 can include a third sensor zone 456 that measures a third scattered or propagated light 456s within a third range of angles relative to the light beam axis 444. As shown here, the third range of angles for scattered or propagated light 456s is different from both the first range of angles for scattered or propagated light 452s and the second range of angles for scattered or propagated light 454s. The light detection assembly 450 also includes a fourth sensor zone 458 that measures axial light 458t transmitted through the cells of the biological sample passing individually through the cell interrogation zone 412 or propagated from the cell interrogation zone along the axis beam. In some instances, each of the sensor zones 452, 454, 456, and 458 are disposed at a separate sensor associated with that specific sensor zone. In some instances, one or more of the sensor zones 452, 454, 456, and 458 are disposed on a common sensor of the light detection assembly 450. For example, the light detection assembly may include a first sensor 451 that includes first sensor zone 452 and second sensor zone 454. Hence, a single sensor may be used for detecting or measuring two or more types (e.g. low angle, medium angle, or high angle) of light scatter or propagation.

Figure 6A:
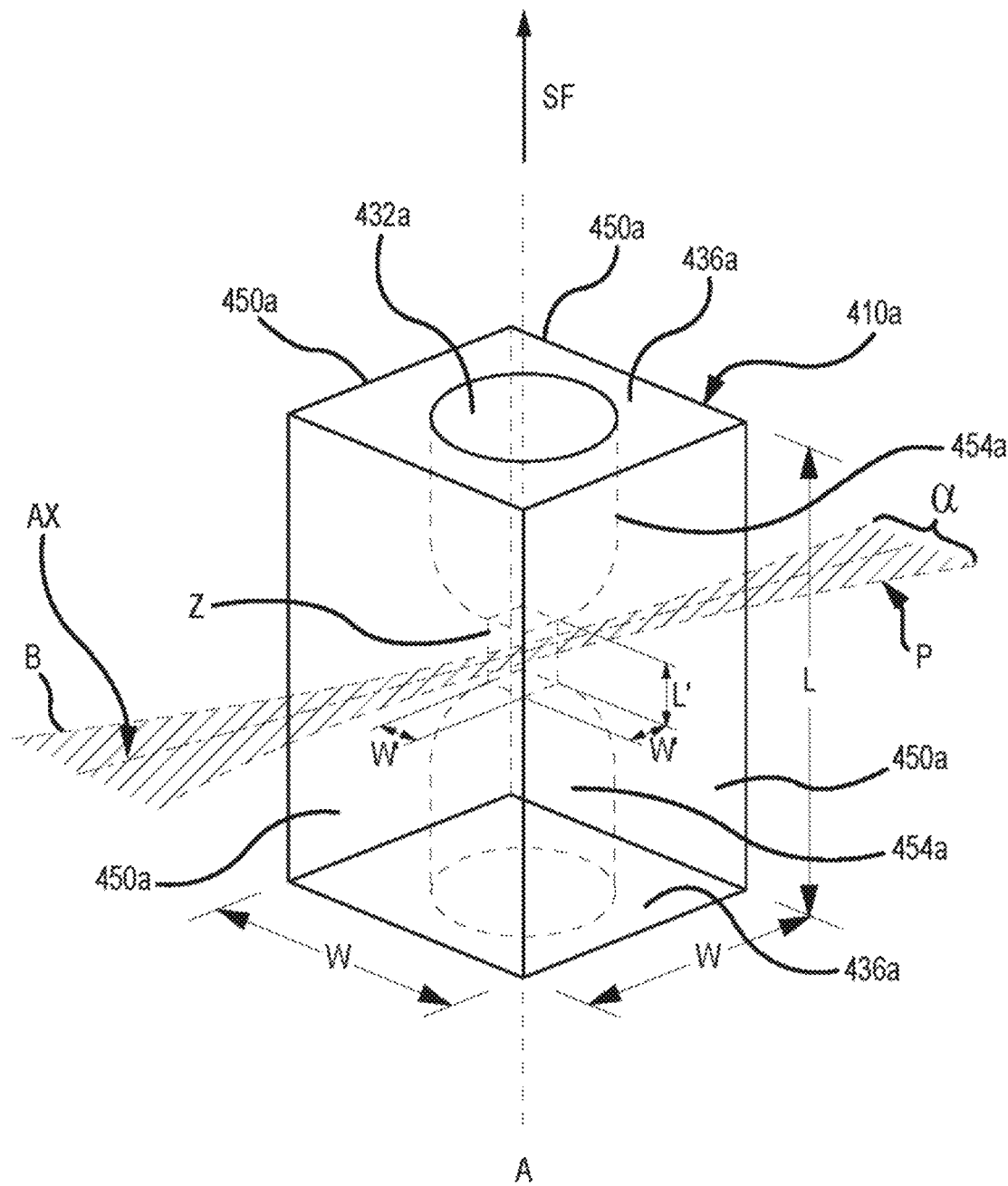
FIG. 6A shows aspects of an optical element of a cellular analysis system according to instances of the present invention.

Automated cellular analysis systems may include any of a variety of optical elements or transducer features. For example, as depicted in FIG. 6A, an optical element 410a of a cellular analysis system transducer may have a square prism shape, with four rectangular, optically flat sides 450a and opposing end walls 436a. In some instances, the respective widths W of each side 450a are the same, each measuring about 4.2 mm, for example. In some instances, the respective lengths L of each side 450a are the same, each measuring about 6.3 mm, for example. In some instances, all or part of the optical element 410a may be fabricated from fused silica, or quartz. A flow passageway 432a formed through a central region of optical element 410a may be concentrically configured with respect to a longitudinal axis A passing through the center of element 410a and parallel to a direction of sample-flow as indicated by arrow SF. Flow passageway 432a includes a cell interrogation zone Z and a pair of opposing tapered bore holes 454a having openings in the vicinity of their respective bases that fluidically communicate with the cell interrogation zone. In some instances, the transverse cross-section of the cell interrogation zone Z is square in shape, the width W' of each side nominally measuring 50 microns±10 microns. In some instances, the length L' of the cell interrogation zone Z, measured along axis A, is about 1.2 to 1.4 times the width W' of the interrogation zone. For example, the length L' may be about 65 microns±10 microns. As noted elsewhere herein, DC and RF measurements can be made on cells passing through the cell interrogation zone. In some instances, the maximum diameter of the tapered bore holes 454a, measured at end walls 436a, is about 1.2 mm. An optical structure 410a of the type described can be made from a quartz square rod containing a 50×50 micron capillary opening, machined to define the communicating bore holes 454a, for example. A laser or other irradiation source can produce a beam B that is directed through or focused into the cell interrogation zone. For example, the beam may be focused into an elliptically shaped waist located within the interrogation zone Z at a location through which the cells are caused to pass. A cellular analysis system may include a light detection assembly that is configured to detect light which emanates from the optical element 410a, for example light P that is propagated from the cell interrogation zone Z which contains illuminated or irradiated cells flowing therewithin. As depicted here, light P can propagate or emanate from the cell interrogation zone Z within an angular range α, and thus can be measured or detected at selected angular positions or angular ranges relative to the beam axis AX. Relatedly, a light detection assembly can detect light scattered or axially transmitted in a forward plane within various angular ranges with respect to an axis AX of beam B. As discussed elsewhere herein, one or more light propagation measurements can be obtained for individual cells passing through the cell interrogation zone one at a time. In some cases, a cellular analysis system may include one or more features of a transducer or cell interrogation zone such as those described in U.S. Pat. Nos. 5,125,737; 6,228,652; 8,094,299; and 8,189,187, the contents of which are incorporated herein by reference.

Figure 7:
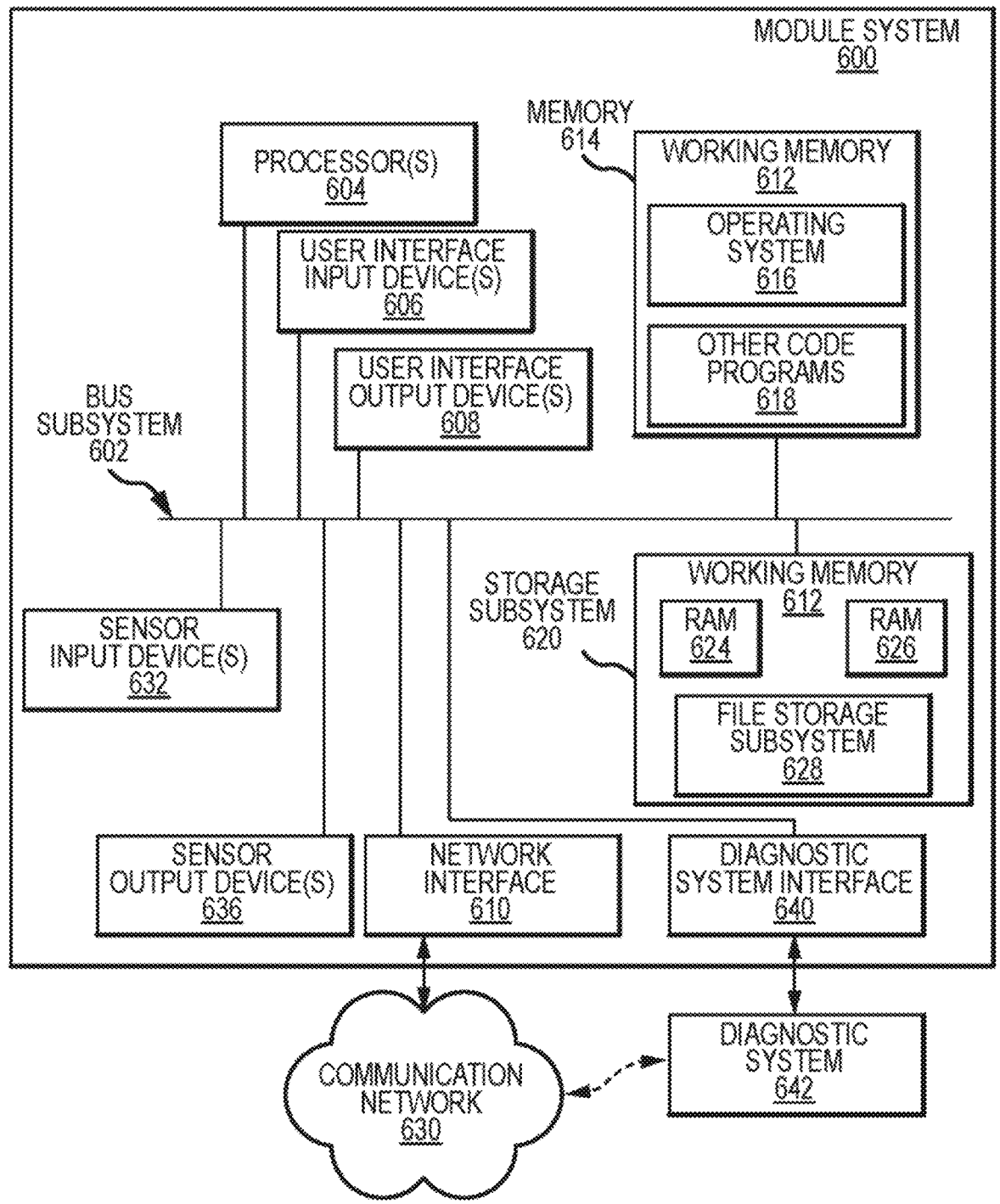
FIG. 7 provides a simplified block diagram of an exemplary module system according to instances of the present invention.

FIG. 7 is a simplified block diagram of an exemplary module system that broadly illustrates how individual system elements for a module system 600 may be implemented in a separated or more integrated manner. Module system 600 may be part of or in connectivity with a cellular analysis system for evaluating the infection status according to embodiments of the present invention. Module system 600 is well suited for producing data or receiving input related to evaluate the infection status. In some instances, module system 600 includes hardware elements that are electrically coupled via a bus subsystem 602, including one or more processors 604, one or more input devices 606 such as user interface input devices, and/or one or more output devices 608 such as user interface output devices. In some instances, system 600 includes a network interface 610, and/or a diagnostic system interface 640 that can receive signals from and/or transmit signals to a diagnostic system 642. In some instances, system 600 includes software elements, for example shown here as being currently located within a working memory 612 of a memory 614, an operating system 616, and/or other code 618, such as a program configured to implement one or more aspects of the techniques disclosed herein. Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing any one or more of the method or process steps described herein.

In some embodiments, module system 600 may include a storage subsystem 620 that can store the basic programming and data constructs that provide the functionality of the various techniques disclosed herein. For example, software modules implementing the functionality of method aspects, as described herein, may be stored in storage subsystem 620. These software modules may be executed by the one or more processors 604. In a distributed environment, the software modules may be stored on a plurality of computer systems and executed by processors of the plurality of computer systems. Storage subsystem 620 can include memory subsystem 622 and file storage subsystem 628. Memory subsystem 622 may include a number of memories including a main random access memory (RAM) 626 for storage of instructions and data during program execution and a read only memory (ROM) 624 in which fixed instructions are stored. File storage subsystem 628 can provide persistent (non-volatile) storage for program and data files, and may include tangible storage media which may optionally embody patient, treatment, assessment, or other data. File storage subsystem 628 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 600. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 628. In some embodiments, the software or code will provide protocol to allow the module system 600 to communicate with communication network 630. Optionally, such communications may include dial-up or internet connection communications.

It is appreciated that system 600 can be configured to carry out various aspects of methods of the present invention. For example, processor component or module 604 can be a microprocessor control module configured to receive cellular parameter signals from a sensor input device or module 632, from a user interface input device or module 606, and/or from a diagnostic system 642, optionally via a diagnostic system interface 640 and/or a network interface 610 and a communication network 630. In some instances, sensor input device(s) may include or be part of a cellular analysis system that is equipped to obtain multiple light angle detection parameters, such as Beckman Coulter's UniCel® DxH™ Cellular Analysis System. In some instances, user interface input device(s) 606 and/or network interface 610 may be configured to receive cellular parameter signals generated by a cellular analysis system that is equipped to obtain multiple light angle detection parameters, such as Beckman Coulter's UniCel® DxH™ Cellular Analysis System. In some instances, diagnostic system 642 may include or be part of a cellular analysis system that is equipped to obtain multiple light angle detection parameters, such as Beckman Coulter's UniCel® DxH™ Cellular Analysis System.

Processor component or module 604 can also be configured to transmit cellular parameter signals, optionally processed according to any of the techniques disclosed herein, to sensor output device or module 636, to user interface output device or module 608, to network interface device or module 610, to diagnostic system interface 640, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, Macintosh, and Unix, along with any of a variety of programming languages, may be used to implement embodiments of the present invention.

User interface input devices 606 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606 may also download a computer executable code from a tangible storage media or from communication network 630, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600.

User interface output devices 606 may include, for example, a display subsystem, a printer, a fax machine, or non-visual displays such as audio output devices. The display subsystem may be a cathode ray tube (CRT), a flat-panel device such as a liquid crystal display (LCD), a light-emitting diode (LED) display, an organic light-emitting diode (OLED) display, a projection device, or the like. The display subsystem may also provide a non-visual display such as via audio output devices. In general, use of the term "output device" is intended to include a variety of conventional and proprietary devices and ways to output information from module system 600 to a user.

Bus subsystem 602 provides a mechanism for letting the various components and subsystems of module system 600 communicate with each other as intended or desired. The various subsystems and components of module system 600 need not be at the same physical location but may be distributed at various locations within a distributed network. Although bus subsystem 602 is shown schematically as a single bus, alternate embodiments of the bus subsystem may utilize multiple busses.

Network interface 610 can provide an interface to an outside network 630 or other devices. Outside communication network 630 can be configured to effect communications as needed or desired with other parties. It can thus receive an electronic packet from module system 600 and transmit any information as needed or desired back to module system 600. As depicted here, communication network 630 and/or diagnostic system interface 642 may transmit information to or receive information from a diagnostic system 642 that is equipped to obtain multiple light angle detection parameters, such as such as Beckman Coulter's UniCel® DxH™ Cellular Analysis System.

In addition to providing such infrastructure communications links internal to the system, the communications network system 630 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 600 itself can be of varying types including a computer terminal, a personal computer, a portable computer, a workstation, a network computer, or any other data processing system. Due to the ever-changing nature of computers and networks, the description of module system 600 depicted in FIG. 7 is intended only as a specific example for purposes of illustrating one or more embodiments of the present invention. Many other configurations of module system 600 are possible having more or less components than the module system depicted in FIG. 7. Any of the modules or components of module system 600, or any combinations of such modules or components, can be coupled with, or integrated into, or otherwise configured to be in connectivity with, any of the cellular analysis system embodiments disclosed herein. Relatedly, any of the hardware and software components discussed above can be integrated with or configured to interface with other medical assessment or treatment systems used at other locations.

In some embodiments, the module system 600 can be configured to receive one or more cellular analysis parameters of a patient at an input module. Cellular analysis parameter data can be transmitted to an assessment module where an infection status is evaluated, predicted, analyzed, or determined. The infection status can be output to a system user via an output module. In some cases, the module system 600 can determine an initial treatment or induction protocol for the patient, based on one or more cellular analysis parameters and/or the evaluated infection status, for example by using a treatment module. The treatment can be output to a system user via an output module. Optionally, certain aspects of the treatment can be determined by an output device, and transmitted to a treatment system or a sub-device of a treatment system. Any of a variety of data related to the patient can be input into the module system, including age, weight, sex, treatment history, medical history, and the like. Parameters of treatment regimens or diagnostic evaluations can be determined based on such data.

Relatedly, in some instances a system includes a processor configured to receive the cell population data as input. Optionally, a processor, storage medium, or both, may be incorporated within a hematology or cellular analysis machine. In some instances, the hematology machine may generate cell population data or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Cell Population Data

In addition to a differential count, once the WBC sub-populations are formed, the mean (MN) and standard deviation (SD) values for the grades of various morphologic parameters (e.g. volume, conductivity, and angles of light scatter or propagation) can be calculated separately for leukocytes and other blood cells. For example, a WBC differential channel can provide measurement data for neutrophils, lymphocytes, monocytes, eosinophils, and/or basophils and an nRBC channel can provide measurement data for non-nucleated red blood cells or a non-nucleated red blood cell parameter, as described elsewhere herein. One of skill in the art will appreciate that neutrophils, eosinophils and basophils are varieties of granulocytes, which are WBCs with cytoplasmic secretory granules. As such, the WBC differential channel can provide measurement data for granulocytes, or for granulocytes other than mast cells. As a result, a vast amount of data directly correlating to blood cell morphology can be generated. This information can be called collectively "Cell Population Data" (CPD). Table 1 depicts a variety of Cell Population Data parameters which may be obtained based on a biological sample of an individual. SD-V-MO may be related to the first cell population distribution width in instances. SD-V-LY may be used as the second cell population distribution width in instances. Instances may exclude any subset of the parameters listed in Table 1. Instances may include or exclude any parameters for basophils. Additionally, instances may include any subset of the parameters listed in Table 1.

TABLE 1

| | Cell Population Data parameters | | | | |
|---|---|---|---|---|---|
| | Neutrophil NE (ne) | Lymphocyte LY (ly) | Monocyte MO (mo or mn) | Eosinophil EO (eo) | Non-nucleated red blood cell NNRBC (nnr or nnrbc) |
| Cell Conductivity (C) high freq. current | SD-C-NE MN-C-NE | SD-C-LY MN-C-LY | SD-C-MO MN-C-MO | SD-C-EO MN-C-EO | SD-C-NNRBC MN-C-NNRBC |
| Cell Volume (V) low freq. current | SD-V-NE MN-V-NE | SD-V-LY MN-V-LY | SD-V-MO MN-V-MO | SD-V-EO MN-V-EO | SD-V-NNRBC MN-V-NNRBC |
| Axial light loss or absorbed light (AL2 or ALL) | SD-AL2-NE MN-AL2-NE | SD-AL2-LY MN-AL2-LY | SD-AL2-MO MN-AL2-MO | SD-AL2-EO MN-AL2-EO | SD-AL2-NNRBC MN-AL2-NNRBC |
| Low-angle light scatter (LALS) | SD-LALS-NE MN-LALS-NE | SD-LALS-LY MN-LALS-LY | SD-LALS-MO MN-LALS-MO | SD-LALS-EO MN-LALS-EO | SD-LALS-NNRBC MN-LALS-NNRBC |
| Upper median-angle light scatter (UMALS) | SD-UMALS-NE MN-UMALS-NE | SD-UMALS-LY MN-UMALS-LY | SD-UMALS-MO MN-UMALS-MO | SD-UMALS-EO MN-UMALS-EO | SD-UMALS-NNRBC MN-UMALS-NNRBC |
| Lower median-angle light scatter (LMALS) | SD-LMALS-NE MN-LMALS-NE | SD-LMALS-LY MN-LMALS-LY | SD-LMALS-MO MN-LMALS-MO | SD-LMALS-EO MN-LMALS-EO | SD-LMALS-NNRBC MN-LMALS-NNRBC |
| Median-angle light scatter (MALS) [UMALS + LMALS] | SD-MALS-NE MN-MALS-NE | SD-MALS-LY MN-MALS-LY | SD-MALS-MO MN-MALS-MO | SD-MALS-EO MN-MALS-EO | SD-MALS-NNRBC MN-MALS-NNRBC |

III. Embodiments

Embodiment 1 may include a method for operating a hematology analyzer, the method comprising: passing a control material through a hematology analyzer, the control material comprising a first cell population and a second cell population; determining, using the hematology analyzer, a first cell population volume measurement; determining, using the hematology analyzer, a second cell population volume measurement; calculating a first value of a first cell population distribution width from the first cell population volume measurement; calculating a second value of a second cell population distribution width from the second cell population volume measurement; comparing the first value to a first reference range; comparing the second value to a second reference range; and classifying an operational status of the hematology analyzer based on the comparison of the first value to the first reference range and based on the comparison of the second value to the second reference range.

Embodiment 2 may include the method of embodiment 1, wherein calculating the first value comprises calculating the standard deviation, coefficient of variation, or a dispersion measurement of the first cell population volume measurement.

Embodiment 3 may include the method of embodiment 1, wherein prior to passing the control material through the hematology analyzer, the first cell population is characterized by a third value of the first cell population distribution width greater than a value of a monocyte distribution width from an individual with an infection.

Embodiment 4 may include the method of embodiment 1, wherein prior to passing the control material through the hematology analyzer, the second cell population is characterized by a third value of the second cell distribution width lower than a value of a monocyte distribution width from a healthy individual.

Embodiment 5 may include the method of embodiment 3, wherein the third value is greater than a clinical cutoff value.

Embodiment 6 may include the method of embodiment 3, wherein the third value is within the first reference range.

Embodiment 7 may include the method of embodiment 4, wherein the third value is within the second reference range.

Embodiment 8 may include the method of embodiment 3, wherein the third value is indicative of a clinical condition.

Embodiment 9 may include the method of embodiment 8, wherein the third value is indicative of an infection.

Embodiment 10 may include the method of embodiment 9, wherein the third value is indicative of systemic inflammatory response syndrome.

Embodiment 11 may include the method of embodiment 9, wherein the third value is indicative of sepsis.

Embodiment 12 may include the method of embodiment 1, wherein the first cell population distribution width comprises a monocyte distribution width.

Embodiment 13 may include the method of embodiment 1, wherein classifying the operational status of the hematology analyzer comprises: classifying the hematology analyzer as operational upon determining that the first value is within the first reference range and determining that the second value is within the second reference range, or classifying the hematology analyzer as not operational upon at least one of determining that the first value is outside the first reference range or determining that the second value is outside the second reference range.

Embodiment 14 may include the method of embodiment 1, further comprising: classifying the hematology analyzer as operational, passing a blood sample from a patient through the hematology analyzer, determining, using the hematology analyzer, a monocyte distribution width in the blood sample, and evaluating an infection status associated with the blood sample based on the determined monocyte distribution width.

Embodiment 15 may include the method of embodiment 14, wherein: evaluating the infection status comprises determining an infection is present, the method further comprising: treating the patient for the infection earlier than conventional methods to decrease the patient's risk of death.

Embodiment 16 may include the method of embodiment 1, further comprising: classifying the operational status as operational, passing the control material again through the hematology analyzer within 24 hours of passing the control material through the hematology analyzer.

Embodiment 17 may include the method of embodiment 1, wherein the first cell population simulates monocytes.

Embodiment 18 may include the method of embodiment 1, wherein the second cell population simulates lymphocytes.

Embodiment 19 may include the method of embodiment 1, wherein the first cell population simulates a cell type selected from the group consisting of monocytes, neutrophils, lymphocytes, eosinophils, basophils, and mixtures thereof.

Embodiment 20 may include the method of embodiment 1, wherein the second cell population simulates a cell type selected from the group consisting of monocytes, neutrophils, monocytes, eosinophils, basophils, and mixtures thereof.

Embodiment 21 may include the method of embodiment 1, wherein the first cell population volume measurement comprises measuring direct current impedance or RF conductivity.

Embodiment 22 may include the method of embodiment 1, further comprising measuring an optical parameter.

Embodiment 23 may include the method of embodiment 22, wherein the optical parameter is a light scatter parameter.

Embodiment 24 may include the method of embodiment 23, wherein the light scatter parameter is selected from a group consisting of upper median angle light scatter (UMALS), lower median angle light scatter (LMALS), median angle light scatter (MALS), and lower angle light scatter (LALS).

Embodiment 25 may include the method of embodiment 1, wherein the first cell population comprises processed alligator red blood cells.

Embodiment 26 may include the method of embodiment 1, wherein the second cell population comprises Goose fixed red blood cells.

Embodiment 27 may include the method of embodiment 1, wherein the control material comprises human, primate, mammalian, avian, fish, or ungulate blood cells.

Embodiment 28 may include an automated system for evaluating an infection status associated with a blood sample obtained from an individual, the system comprising: a transducer for obtaining current data for a control material as the control material passes through an aperture, the control material comprising a first cell population and a second cell population; a processor; and a non-transitory computer readable medium storing a plurality of instructions that when executed by the processor, cause the system to: obtain current data for the control material, determine a first cell population volume measurement, using the current data, determine a second cell population volume measurement using the current data, calculate a first value of a first cell population distribution width from the first cell population volume measurement, calculate a second value of a second cell population distribution width from the second cell population volume measurement, compare the first value to a first reference range, compare the second value to a second reference range, and classify an operational status of the automated system based on the comparison of the first value to the first reference range and based on the comparison of the second value to the second reference range.

Embodiment 29 may include the automated system of embodiment 28, further comprising: a scanner, wherein the plurality of instructions further cause the system to: identify, using the scanner, a container with the control material as containing the control material.

Embodiment 30 may include the automated system of embodiment 28, wherein the plurality of instructions further cause the system to perform any of the methods in embodiments 2 to 27.

Embodiment 31 may include the automated system of embodiment 28, wherein the first cell population or the second cell population simulates granulocytes.

Embodiment 32 may include the method of embodiment 19 or embodiment 20, wherein the cell population simulates granulocytes.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. An automated system for evaluating an infection status associated with a blood sample obtained from an individual, the automated system comprising:
    a transducer operable to measure a control material as the control material passes through an aperture, the control material comprising a first cell population and a second cell population, wherein the first cell population is different from the second cell population;
    a processor; and
    a non-transitory computer readable medium storing a plurality of instructions that when executed by the processor, cause the automated system to:
        obtain current data for the control material,
        calculate a first value, wherein the first value is a distribution width value of the first cell population,
        calculate a second value, wherein the second value is a distribution width value of the second cell population,
        perform a first comparison for a hematology parameter by comparing the first value to a first reference range for the hematology parameter,
        perform a second comparison for the hematology parameter by comparing the second value to a second reference range for the hematology parameter, and
        classify an operational status of the automated system based on the first comparison and the second comparison.

2. The automated system of claim 1, wherein calculating the first value comprises calculating a standard deviation, coefficient of variation, or a dispersion measurement of a volume measurement measuring volumes of individual cells from the first cell population.

3. The automated system of claim 1, wherein:
    the hematology parameter is monocyte distribution width; and
    the control material has a known monocyte distribution width value greater than a value of a monocyte distribution width from a healthy individual.

4. The automated system of claim 1, wherein:
    the hematology parameter is monocyte distribution width; and
    the control material has a known monocyte distribution width value lower than a value of a monocyte distribution width from an individual with an infection.

5. The automated system of claim 3, wherein the first value is indicative of a clinical condition.

6. The automated system of claim 5, wherein the first value is indicative of an infection.

7. The automated system of claim 5, wherein the first value is indicative of systemic inflammatory response syndrome.

8. The automated system of claim 5, wherein the first value is indicative of sepsis or a likelihood of developing sepsis.

9. A method for operating a hematology analyzer, the method comprising:
    passing a control material through the hematology analyzer, the control material comprising a first cell population and a second cell population, wherein the first cell population is different from the second cell population;
    calculating a first value, wherein the first value is a distribution width value of the first cell population;
    calculating a second value, wherein the second value is a distribution width value of the second cell population;
    performing a first comparison for a hematology parameter by comparing the first value to a first reference range for the hematology parameter;
    performing a second comparison for the hematology parameter by comparing the second value to a second reference range for the hematology parameter; and
    classifying an operational status of the hematology analyzer based on the first comparison and the second comparison.

10. The method of claim 9, wherein classifying the operational status of the hematology analyzer comprises:
    classifying the hematology analyzer as operational upon determining that the first value is within the first reference range and determining that the second value is within the second reference range.

11. The method of claim 9, wherein:
    the hematology parameter is monocyte distribution width;
    the method comprises:
        classifying the operational status of the hematology analyzer comprises classifying the hematology analyzer as operational,
        passing a blood sample from a patient through the hematology analyzer,
        determining, using the hematology analyzer, a monocyte distribution width value for the blood sample, and
        evaluating an infection status associated with the blood sample based on the monocyte distribution width value for the blood sample.

12. The method of claim 11, wherein evaluating the infection status comprises determining an infection is present, and the method further comprises treating the patient for the infection earlier than conventional methods.

13. The method of claim 9, further comprising:
    classifying the operational status as operational, passing the control material again through the hematology analyzer within 24 hours of passing the control material through the hematology analyzer.

14. The method of claim 9, wherein the first cell population simulates a cell type selected from the group consisting of monocytes, neutrophils, lymphocytes, eosinophils, basophils, and mixtures thereof.

15. The method of claim 9, wherein the second cell population simulates a cell type selected from the group consisting of monocytes, neutrophils, monocytes, eosinophils, basophils, and mixtures thereof.

16. The method of claim 9, wherein the first cell population volume measurement comprises measuring direct current impedance or radio frequency (RF) conductivity.

17. The method of claim 9, further comprising measuring an optical parameter.

18. The method of claim 17, wherein the optical parameter is a light scatter parameter.

19. The method of claim 18, wherein the light scatter parameter is selected from a group consisting of upper median angle light scatter (UMALS), lower median angle light scatter (LMALS), median angle light scatter (MALS), and lower angle light scatter (LALS).

20. The method of claim 9, wherein the first cell population or the second cell population simulates a granulocyte.

21. The method of claim 9, wherein:
the hematology parameter is a numerical characteristic of a first cell type;
the first cell population comprises cells of a second cell type;
the second cell population comprises cells of a third cell type;
the first cell type, the second cell type, and the third cell type are all different from each other; and
classifying the operational status of the hematology analyzer based on the first comparison and the second comparison comprises validating the analyzer's ability to operate over a range of values for the hematology parameter sufficient to identify a clinical condition using the hematology parameter.

22. The method of claim 21, wherein:
the first cell type is human monocytes;
the hematology parameter is monocyte distribution width; and
neither the second cell type nor the third cell type is a human cell type.

23. A method for operating a hematology analyzer, the method comprising:
passing a control material through the hematology analyzer, the control material comprising a first cell population and a second cell population, wherein the first cell population is different from the second cell population;
calculating a first value, wherein the first value is a distribution width value of the first cell population;
calculating a second value, wherein the second value is a distribution width value of the second cell population;
performing a first comparison for a hematology parameter by comparing the first value to a first reference range for the hematology parameter;
performing a second comparison for the hematology parameter by comparing the second value to a second reference range for the hematology parameter; and
classifying an operational status of the hematology analyzer based on the first comparison and/or the second comparison, wherein classifying the operational status of the hematology analyzer comprises classifying the hematology analyzer as not operational upon at least one of determining that the first value is outside the first reference range or determining that the second value is outside the second reference range.

* * * * *